(12) United States Patent
Grunstein et al.

(10) Patent No.: US 6,630,140 B1
(45) Date of Patent: *Oct. 7, 2003

(54) COMPOSITIONS AND METHODS FOR TREATMENT OF ASTHMA

(75) Inventors: Michael M. Grunstein, Merion, PA (US); Hakon Hakonarson, Reykjavic (IS)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/261,104

(22) Filed: Mar. 3, 1999

Related U.S. Application Data
(60) Provisional application No. 60/077,398, filed on Mar. 10, 1998.

(51) Int. Cl.<sup>7</sup> ........................ A61K 39/395; A61K 38/00
(52) U.S. Cl. ................................ 424/133.1; 424/143.1; 514/2
(58) Field of Search ...................... 536/23.1; 530/300, 530/350, 388.22; 514/44, 810, 2, 826; 424/130.1, 133.1, 143.1; 436/506, 507, 826; 435/7.1, 7.2, 7.21, 7.8

(56) References Cited

U.S. PATENT DOCUMENTS

| | | | |
|---|---|---|---|
| 5,676,930 A | * | 10/1997 | Jager et al. .................... 424/45 |
| 5,994,514 A | * | 11/1999 | Jardieu et al. ......... 530/388.22 |
| 6,011,138 A | * | 1/2000 | Reff et al. ............. 530/388.22 |
| 6,019,968 A | * | 2/2000 | Platz et al. .............. 424/130.1 |

FOREIGN PATENT DOCUMENTS

| | | | | |
|---|---|---|---|---|
| WO | 95/02693 | * | 2/1996 | |
| WO | WO96/12741 | * | 5/1996 | |
| WO | WO 97/04807 | * | 2/1997 | |
| WO | WO 00/72879 A1 | * | 12/2000 | .......... A61K/39/35 |

OTHER PUBLICATIONS

Kay et al. "Gene Therapy" Proc. Natl. Acad. Sci. USA vol. 94, pp. 12744–12746, 1997.*
Aubry et al., 1992, Nature 358:505–507.
Bai, 1990 Am. Rev. Respir. Dis. 141:552–557.
Barbas, 1995, Nature Medicine 1:837–839.
Barnes et al., 1988, Pharmacol. Rev. 40:49–84.
Beasley et al., 1989, Am. Rev. Respir. Dis. 139:806–817.
Beaven and Metzger, 1993, Immunol. Today 14:222–226.
Borish et al., 1991, J. Immunol. 146:63–67.
Burrows et al., 1995, J. Allergy Clin. Immunol. 95:548–556.
Burrows et al., 1995, Am. J. Respir. Crit. Care Med. 152:1497–1500.
Burrows et al., 1992, N. Engl. J. Med. 326:560–561.
Burton et al., 1994, Adv. Immunol. 57:191–280.
Capel et al., 1994, Immunometh. 4:25–34.
Capron et al., 1984, J. Immunol. 132:462–468.
Chihara et al., 1991, Annal. Allergy. 67:429.
Chomczynski and Sacchi, 1987, Anal. Biochem. 162:156–159.
Cohen,1993, Science 259:1691–1692.
Conroy et al., 1977, J. Immunol. 118:1317–1321.
Coyle et al., 1996, J. Exp. Med. 183:1303–1310.
Cranage et al., 1986, EMBO J. 5:3057–3063.
Daeron and Ishizaka, 1986, J. Immunol. 136:1612–1619.
de Kruif et al., 1995, J. Mol. Biol. 248:97–105.
Delespease et al., 1992, Immunol. Rev. 125:78–97.
Fynan et al.,1993, Proc. Natl. Acad. Sci. U.S.A. 90:11478–11482.
Gagro et al., 1993, Int. Arch. Allergy. Immunol. 101:203–208.
Galli, 1993, N. Engl. J. Med. 328:257–265.
Goldie et al., 1986, Br. J. Clin. Pharmacol. 22:669–676.
Hakonarson et al., 1995, Am. J. Physiol. (Lung Cell Mol. Physiol.) 269:L645–L652.
Hakonarson et al., 1997, J. Clin. Invest. 99:117–124.
Hakonarson et al., 1996, J. Clin. Invest. 97:2593–2600.
Joseph et al., 1983, J. Clin. Invest. 71:221–230.
Kay, 1991, J. Allergy Clin. Immunol. 87:893.
Kay et al., 1997, Proc. Natl. Acad. Sci. U.S.A. 94:12744–12746.
Kessler, 1975, J. Immunol. 115:1617–1624.
Kikutani et al., 1986, Cell 47:657–665.
Lantz et al., 1997, Am. Assoc. of Immun. 2517–2521.
Lee et al., 1987, J. Immunol. 139:1191–1198.
Lee and Conrad, 1986, J. Immunol. 136:4573–4580.
Litchfield and Lee, 1992, J. Asthma. 29:181–191.
Malveaux et al., 1978, J. Clin. Invest 62:176–181.
Marks et al., 1991, J. Mol. Biol. 222:581–597.
Matsumoto et al., 1991, J. Exp. Med. 173:55–64.
Matsumoto et al., 1987, Annal. Allergy. 58:261.
McFadden et al., 1994, Am. J. Respir. Crit. Care Med. 150:523–526.
McKenzie et al., 1994, Current Opinion in Hematology 1:45–52.
Metzger, 1992, Immunol. Rev. 125:37–48.
Mossalayi et al., 1002, EMBO J. 11:4323–4328.
Noveral et al., 1992, Am. J. Physiol. (Lung Cell. Mol. Physiol.) 263:L555–L561.
Pearce et al., 1990, Thorax 45:170–175.
Putney et al., 1983, Nature 302:718–721.
Rabatic et al., 1993, Exp. Immunol. 94:337–340.
Sears et al., 1991, N. Engl. J. Med. 325:1067–1071.
Seshadri et al., 1993, J. Biol. Chem. 268:18474–18480.
Spiegelberg and Simon, 1981, J. Clin. Invest. 68:845–852.
Sutton and Gould, 1993, Nature 366:421–428.
Tanaka and Grunstein, 1990, J. Clin. Invest. 85:345–350.

(List continued on next page.)

Primary Examiner—Marjorie Moran
(74) Attorney, Agent, or Firm—Dann, Dorfman, Herrell and Skillman

(57) ABSTRACT

Methods of treating or preventing induction of asthma in a human patient are provided. The methods comprise administering to the human an anti-FcεRII receptor protein ligand suspended in a pharmaceutically acceptable carrier in an amount sufficient to inhibit binding of IgE to an anti-FcεRII receptor protein thereby treating or preventing induction of asthma in the human.

24 Claims, 15 Drawing Sheets

OTHER PUBLICATIONS

Walker et al., 1992, Am. Rev. Respir. Dis. 146:109–115.
Watson et al., 1993, Am. J. Respir. Cell Mol. Biol. 8:365–369.
Weenink et al., 1997, International Immunol. 9(6):889–896.
William et al., 1992, J. Immunol. 149:2823–2829.
Wolff et al.,1991, Biotechniques 11:474–485.
Wright et al., 1992, Critical Rev. in Immunol. 12(3,4):125–168.
Yamaguchi et al., 1997, J. Exp. Med. 185:663–672.

* cited by examiner

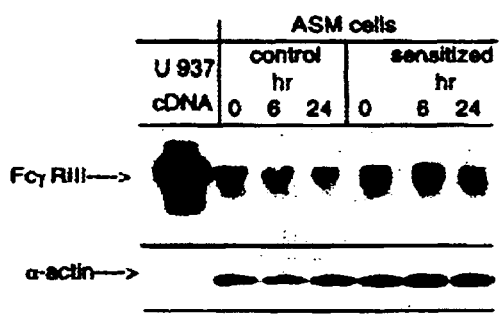
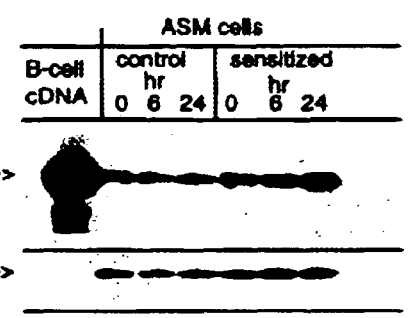
Fig. 5A
Fig. 5B

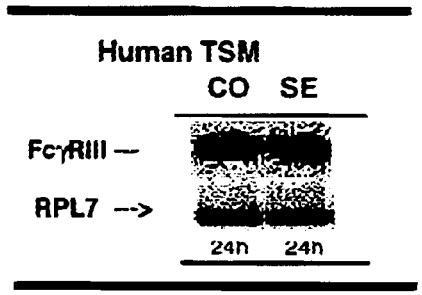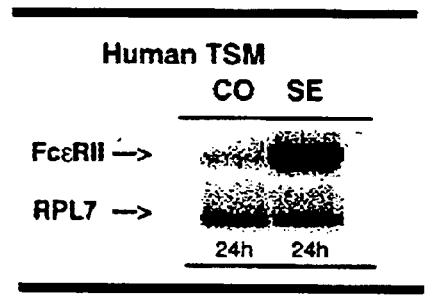
Fig. 6A
Fig. 6B

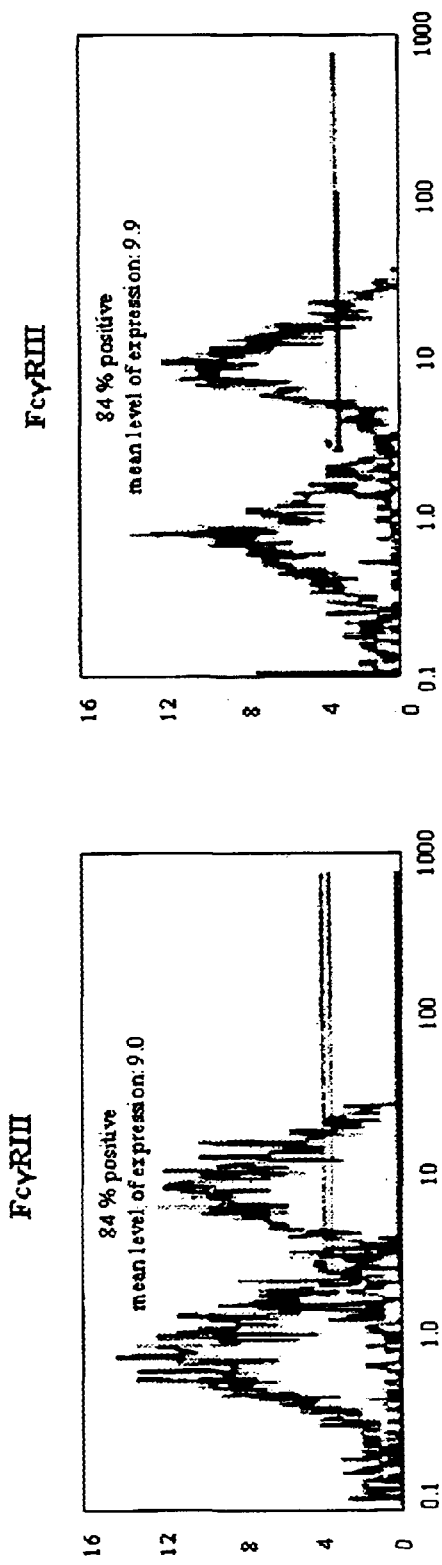
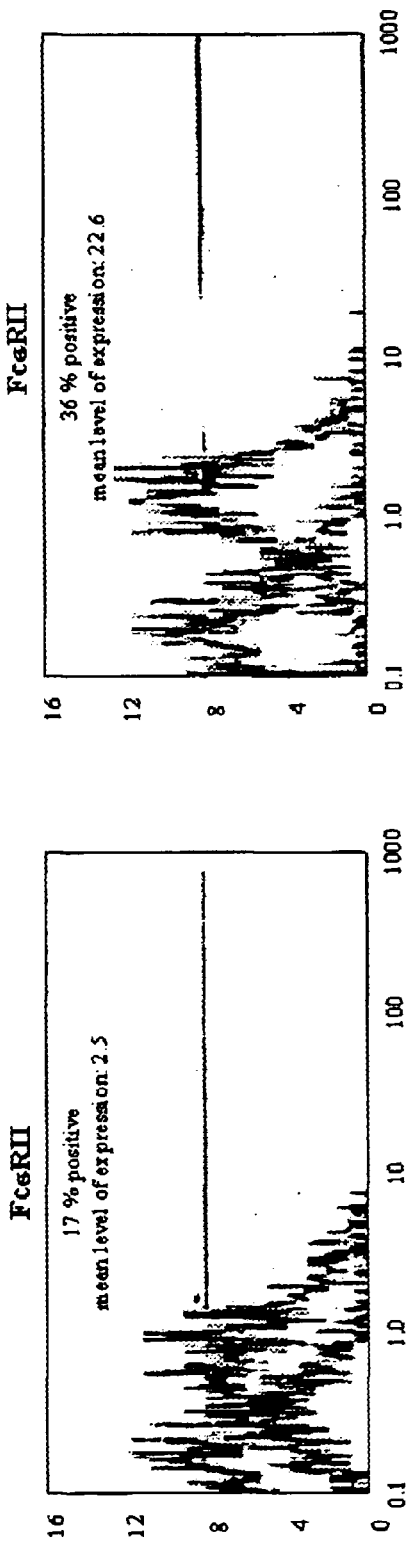
Fig. 9A
Fig. 9B

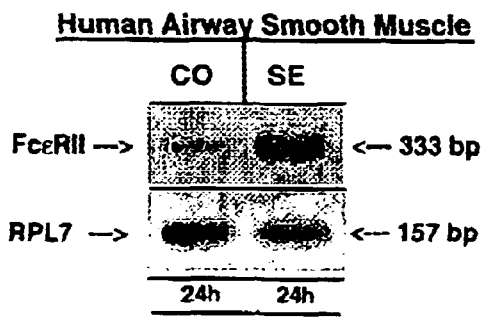
Fig. 13
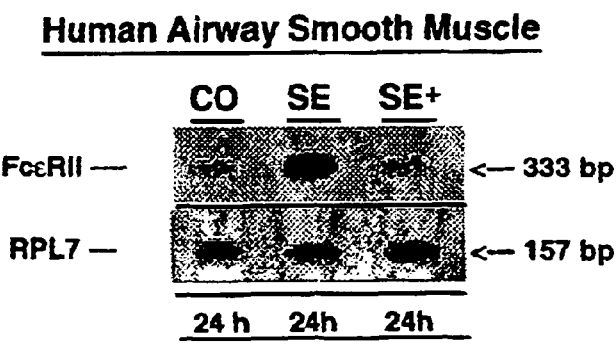
Fig. 14A
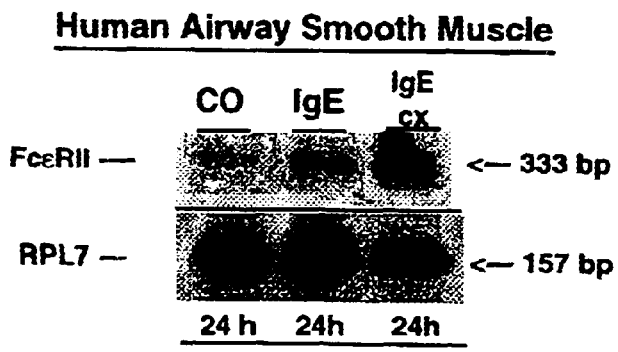

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 1
atgtggttct tgacaactct gctc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 2
atgtctgtct tcttgaaggc tgga                                          24

<210> SEQ ID NO 3

-continued

```
<211> LENGTH: 20
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 3
gactccattc agtggttcca                                              20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 4
gtcagctgtt tcatagtcat tg                                           22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 5
gactccattc agtggttcca                                              20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 6
cccaactttg tcagcctcat c                                            21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 7
aagatctccc aaaggctgtg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 8
atggacttct agctgcaccg                                              20

<210> SEQ ID NO 9
<211> LENGTH: 19
```

<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 9
cgtctctcaa gtttccaag                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Human Fc
      receptor PCR primer

<400> SEQUENCE: 10
gcacttccgt tgggaatttg                                             20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Rabbit
      alpha-actin PCR primer

<400> SEQUENCE: 11
cgacatcaag gagaagctg                                              19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Rabbit
      alpha-actin PCR primer

<400> SEQUENCE: 12
ctagaagcat ttgcggtgc                                              19

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Human
      ribosomal protein L7 PCR primer

<400> SEQUENCE: 13
aagaggctct cattttcctg gctg                                        24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Human
      ribosomal protein L7 PCR primer

<400> SEQUENCE: 14
tccgttcctc cccataatgt tcc                                         23

<210> SEQ ID NO 15
<211> LENGTH: 20
<212> TYPE: DNA

```
-continued

<213> ORGANISM: Artificial Sequence
<220> FEATURE:
<223> OTHER INFORMATION: Description of Artificial Sequence: Human  Fc
      receptor PCR primer

<400> SEQUENCE: 15
ggaacgggaa ttaccatcct                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Human  Fc
      receptor PCR primer

<400> SEQUENCE: 16
aaagacgatc atcgggaacc                                              20
```

COMPOSITIONS AND METHODS FOR TREATMENT OF ASTHMA

CROSS-REFERENCE TO RELATED APPLICATIONS

This application claims priority, under 35 U.S.C. §119(e), U.S. Provisional Application No. 60/077,398, filed on Mar. 10, 1998, which is hereby incorporated herein by reference in its entirety.

STATEMENT REGARDING FEDERALLY SPONSORED RESEARCH OR DEVELOPMENT

This invention was made in part using funds obtained from the U.S. Government (National Heart, Lung, and Blood Institute Grant Nos. HL-31467 and HL-58245) and the U.S. Government may therefore have certain rights in the invention.

BACKGROUND OF THE INVENTION

The present invention relates to asthma therapy.

Bronchial asthma in mammals is characterized by inflammation of the airways, exaggerated airway reactivity to bronchoconstrictor agonists, and attenuated beta-adrenoceptor-mediated airway relaxation (Bai, 1990 Am. Rev. Respir. Dis. 141:552–557; Goldie et al., 1986, Br. J. Clin. Pharmacol. 22:669–676; McFadden et al., 1994, Am. J. Respir. Crit. Care Med. 150:523–526). In humans with atopic asthma, mast cell activation has been implicated in mediating the immediate bronchoconstrictor response which acutely follows antigen inhalation. This response is a process which involves IgE-mediated activation of the high affinity IgE receptor (FcεRI), leading to cellular degranulation and the release of various mast cell-derived mediators including histamine, eicosanoids, and specific cytokines (Metzger, 1992, Immunol. Rev. 125:37–48; Beaven et al., 1993, Immunol. Today 14:222–226; Galli, 1993, N. Engl. J. Med. 328:257–265). The identification of Fc receptors on other cell types in the lung (e.g., mononuclear cells, eosinophils, and dendritic cells) suggests that, apart from mast cells per se, these other cell types may also serve to propagate the pro-inflammatory allergic pulmonary response, most likely via the orchestrated extended release of various cytokines (Walker et al., 1992, Am. Rev. Respir. Dis. 146:109–115; Watson et al., 1993, Am. J. Respir. Cell Mol. Biol. 8:365–369; Capron et al., 1984, J. Immunol. 132:462–468; Beasley et al., 1989, Am. Rev. Respir. Dis. 139:806–817; Litchfield et al., 1992, J. Asthma 29:181–191; Barnes et al., 1988, Pharmacol. Rev. 40:49–84; Borish et al., 1991, J. Immunol. 146:63–67. It is believed that immune complex/Fc receptor interactions expressed by these cells, i.e., mononuclear cells, eosinophils, and dendritic cells, potentially underlie the progression of the airway inflammatory and bronchoconstrictor responses in asthma, wherein the immediate bronchoconstriction accompanying antigen exposure is followed by the development of the late phase asthmatic response involving various proinflammatory cells. Indeed, recent studies have demonstrated that expression of the inducible form of the low affinity IgE receptor (FcεRII or CD23) is upregulated on monocytes and alveolar macrophages (Williams et al., 1992, J. Immunol.149:2823–2829), as well as on circulating B lymphocytes (Gagro et al., 1993, Int. Arch. Allergy Immunol. 101:203–208; Rabatic et al., 1993, Exp. Immunol. 94:337–340) isolated from atopic asthmatic subjects. Similarly, exposure of asthmatic subjects to allergen and treatment of isolated monocytes with specific cytokines have been shown to up-regulate FcεRII expression on mononuclear phagocytes (Williams et al., 1992, J. Immunol. 149:2823–2829; Joseph et al., 1983, J. Clin. Invest. 71:221–230). These findings suggest that altered Fc receptor expression and action in some cell types may contribute to the overall pro-inflammatory asthmatic response. While it is known that exposure of isolated rabbit and human airway smooth muscle (ASM) to atopic asthmatic serum induces the autocrine release and action of specific cytokines (notably IL-1β) by the sensitized ASM cells (Hakonarson et al., 1997, J. Clin. Invest. 99:117–124), the mechanism by which this sensitization is mediated has not been disclosed.

Current treatment options for asthma include medications that control the airway inflammatory component of the disease, e.g., primarily corticosteroids, sodium cromolyn, methylxanthines, leukotriene modifiers) and rapid relief medications that counteract bronchospasm, e.g., primarily beta-adrenergic agents. There are several disadvantages to using these medications as follows. There is a potential lack of effective sustained action; there are side effects associated with prolonged use of these medications, particularly in the case of corticosteroids and beta-adrenergic agents; there is a progressive loss of sensitivity to these treatments after prolonged use; there is limited efficacy of any of these agents in severe cases of asthma; these agents are non-selective, i.e., they do not specifically target the lung, therefore, side-effects affecting other organs are a potential risk. Furthermore, there are data which document an increased risk of dying from bronchial asthma following prolonged treatment of asthma using long-acting beta-adrenergic agents such as fenoterol (Pearce et al., 1990, Thorax 45:170–175; Spitzer et al., 1992, N. Engl. J. Med. 326:560–561).

Approximately fifteen million individuals in the U.S. have asthma and the disease is the cause of more than five thousand deaths annually in the U.S. In children, asthma represents the most prevalent chronic disease, requiring the most frequent use of emergency room visits and hospitalizations. The overall annual cost for asthma care in the U.S. is estimated to be in the range of billions of dollars. Asthma is the most common cause of school and work absenteeism in the U.S.

There is thus a long felt need for additional and more specific and effective compositions and methods for treatment of asthma which additional compositions and methods overcome the deficiencies of the prior art compositions and methods.

BRIEF SUMMARY OF THE INVENTION

The invention relates to a method of preventing induction of an asthmatic state in a human patient comprising administering to the human an anti-FcεRII receptor protein ligand suspended in a pharmaceutically acceptable carrier in an amount sufficient to inhibit binding of IgE to an FcεRII receptor protein thereby preventing induction of the asthmatic state in the human. Preferably, the pharmaceutically acceptable carrier is physiological saline.

In one aspect, the ligand is selected from the group consisting of an isolated protein, an isolated polypeptide and a non-peptide.

In a preferred embodiment, the ligand is selected from the group consisting of a polyclonal antibody, a monoclonal antibody, a synthetic antibody, a chimeric antibody and a humanized antibody. Preferably, the anti-FcεRII receptor protein ligand is an anti-FcεRII receptor protein antibody.

In another aspect, the ligand is administered to the human in the form of an isolated DNA encoding and capable of expressing the ligand. The DNA may be formulated in a viral or a non-viral vector. When the DNA is formulated in a viral vector, the viral vector is selected from the group consisting of a recombinant vaccinia virus, a recombinant adenovirus, a recombinant retrovirus, a recombinant adeno-associated virus and a recombinant avian pox virus. When the DNA is formulated in a non-viral vector, the non-viral vector is selected from the group consisting of a liposome and a polyamine conjugated DNA.

In yet another aspect, the anti-FcεRII receptor protein ligand is administered to the human in an amount between about 1 ng/kg and about 100 mg/kg of patient body weight.

The invention also relates to a method of treating asthma in a human patient comprising administering to the human an anti-FcεRII receptor protein ligand suspended in a pharmaceutically acceptable carrier in an amount sufficient to inhibit binding of IgE to an FcεRII receptor protein thereby treating asthma in the human. Preferably, the pharmaceutically acceptable carrier is physiological saline.

In one aspect, the ligand is selected from the group consisting of an isolated protein, an isolated polypeptide and a non-peptide.

In a preferred embodiment, the ligand is selected from the group consisting of a polyclonal antibody, a monoclonal antibody, a synthetic antibody, a chimeric antibody and a humanized antibody. Preferably, the anti-FcεRII receptor protein ligand is an anti-FcεRII receptor protein antibody.

In another aspect, the ligand is administered to the human in the form of an isolated DNA encoding and capable of expressing the ligand. The DNA may be formulated in a viral or a non-viral vector. When the DNA is formulated in a viral vector, the viral vector is selected from the group consisting of a recombinant vaccinia virus, a recombinant adenovirus, a recombinant retrovirus, a recombinant adeno-associated virus and a recombinant avian pox virus. When the DNA is formulated in a non-viral vector, the non-viral vector is selected from the group consisting of a liposome and a polyamine conjugated DNA.

In yet another aspect, the anti-FcεRII receptor protein ligand is administered to the human in an amount between about 1 ng/kg and about 100 mg/kg of patient body weight.

Also included in the invention is a method of treating a human having asthma comprising administering to the human a pharmaceutically effective amount of an isolated nucleic acid encoding an anti-FcεRII receptor protein ligand, wherein the nucleic acid expresses the ligand in vivo in an amount sufficient to treat the asthma.

In addition, the invention includes a method of identifying an anti-FcεRII receptor protein ligand comprising providing a mixture comprising IgE and a population of cells which express an FcεRII receptor protein, incubating the mixture in the presence or absence of a test ligand, and measuring the level of IgE bound to the FcεRII receptor protein, wherein a lower level of IgE bound to the cells in the presence of the test compound compared with the level of binding of IgE to the cells in the absence of the test compound is an indication that the test compound is an anti-FcεRII receptor protein ligand.

In a preferred embodiment of this aspect of the invention, the cells are airway smooth muscle cells.

The invention also includes a ligand useful for inhibiting binding of IgE to an FcεRII receptor protein identified by a method comprising providing a mixture comprising IgE and a population of cells which express an FcεRII receptor protein, incubating the mixture in the presence or absence of a test ligand, and measuring the level of IgE bound to the FcεRII receptor protein, wherein a lower level of IgE bound to the cells in the presence of the test compound compared with the level of binding of IgE to the cells in the absence of the test compound is an indication that the test compound is an anti-FcεRII receptor protein ligand.

In addition, the invention includes a method of inhibiting binding of IgE to an FcεRII receptor protein expressed on a cell comprising administering to the cell an anti-FcεRII receptor protein ligand.

The invention also includes a method of regulating production of interleukin-1β in a cell. The method comprises contacting a cell with an anti-FcεRII receptor protein ligand in an amount sufficient to inhibit binding of IgE to an anti-FcεRII receptor protein thereby regulating production of interleukin-1β in a cell.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

Figure 4:
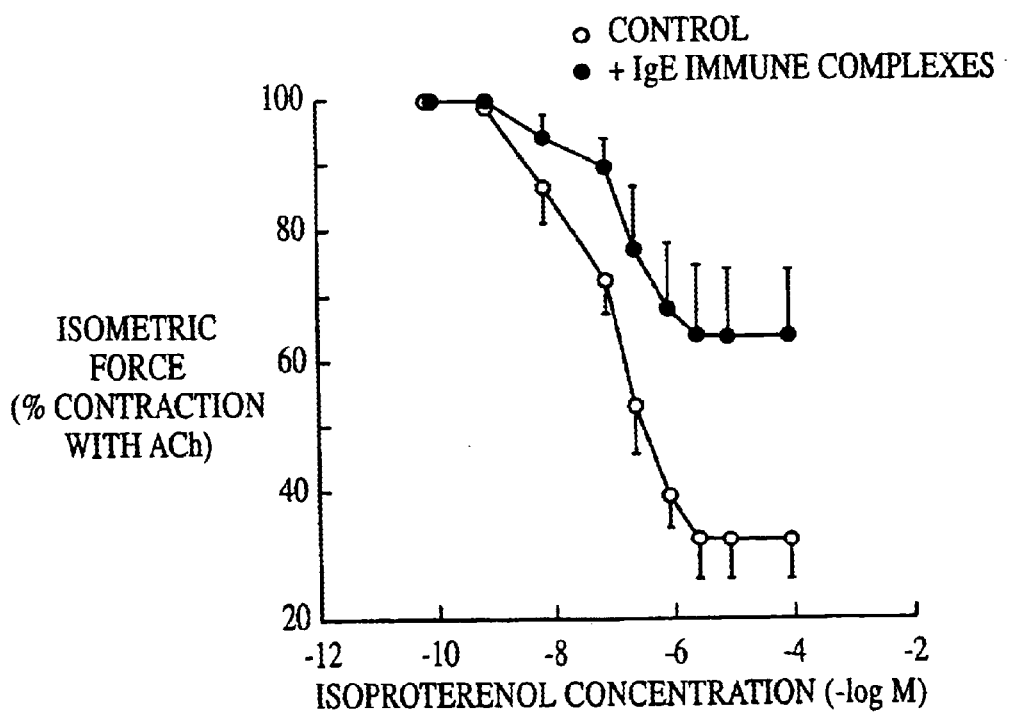

FIG. 4 is a graph depicting a comparison of airway relaxation responses to isoproterenol in paired TSM segments in the absence (open symbols) and presence (filled symbols) of IgE immune complexes. All TSM segments were initially half-maximally contracted with their respective $ED_{50}$ doses of ACh prior to isoproterenol administration. Data represent mean±SE values from 8 paired tissue samples.

FIG. 5A is an image of a gel depicting expression of FcγRIII receptor mRNA using reverse transcriptase polymerase chain reaction (RT-PCR) in rabbit ASM cells following 0, 6 and 24 hours of treatment with 10% control serum and 10% atopic asthmatic sensitizing serum. Expression of α-actin was used to control for loading. cDNA obtained from activated U937 cells (i.e., for FcγRIII) was used as a positive control. The blots were probed with human specific FcγRIII $^{32}$P-labeled cDNA probes.

FIG. 5B is an image of a gel depicting expression of FcεRII receptor mRNA using RT-PCR in rabbit ASM cells following 0, 6 and 24 hours of treatment with 10% control serum and 10% atopic asthmatic sensitizing serum. Expression of α-actin was used to control for loading. cDNA obtained from the immortalized human B-cell line 8.1.6 (i.e., for FcεRII) was used as a positive control. The blots were probed with human specific FcεRII $^{32}$P-labeled cDNA probes.

FIG. 6A is an image of a Southern blot probed with full length FcγRIII and a 157-bp RPL7 human cDNA probe. Paired human airway smooth muscle samples were incubated with control (CO) or atopic asthmatic (SE) serum for 24 hours. cDNA was transcribed from total RNA primed with oligo(dT). PCR products were amplified using a human-specific FcγRIII and RPL7 primers, run on 1.2% agarose gels, transferred to a Zeta-probe membrane and then probed.

FIG. 6B is an image of a Southern blot probed with full length FcεRII and a 157-bp RPL7 human cDNA probe. Paired human airway smooth muscle samples were incubated with control (CO) or atopic asthmatic (SE) serum for 24 hours. cDNA was transcribed from total RNA primed with oligo(dT). PCR products were amplified using human-specific FcεRII and RPL7 primers, run on 1.2% agarose gels, transferred to a Zeta-probe membrane and then probed.

Figure 7:
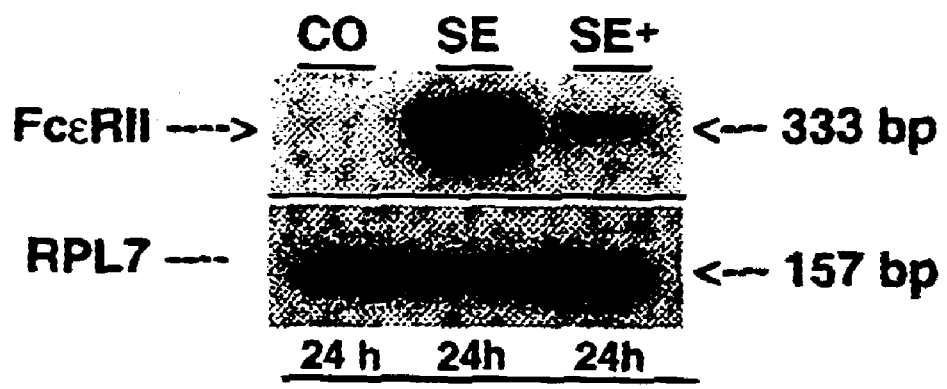

FIG. 7 is an image of a gel depicting the expression of FcεRII mRNA as assessed by RT-PCR in human bronchial smooth muscle tissue following 24 hours of treatment with control (CO) or atopic asthmatic serum in the absence (SE) and presence (SE+) of anti-CD23 MAb. The products of the RT-PCR reactions using 2.5 μg of total RNA and human-specific primers for the FcεRII receptor mRNA are shown. Expression of RPL7 was used to control for gel loading. The blot was probed with the above $^{32}$P-labeled human-specific FcεRII and RPL7 cDNA probes.

Figure 8A:
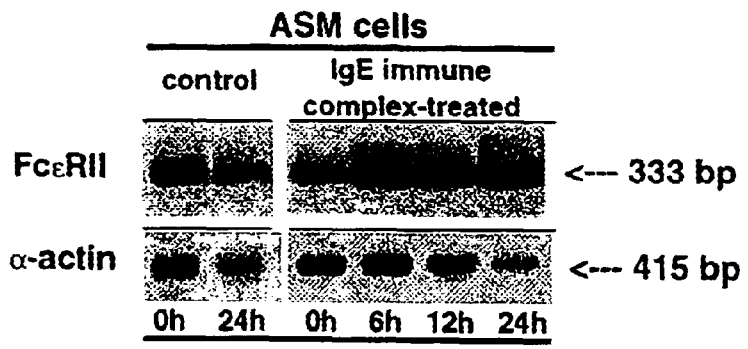

FIG. 8A is an image of a gel depicting the expression of FcεRII as assessed by RT-PCR in rabbit ASM cells following 0 and 24 hours treatment with media alone (control) or with IgE immune complexes for 0, 6, 12 and 24 hours. The products of RT-PCR reactions using 2.5 μg of total RNA and human-specific primers for the FcεRII receptor mRNA are shown. mRNA expression of α-actin is also shown for comparison.

Figure 8B:
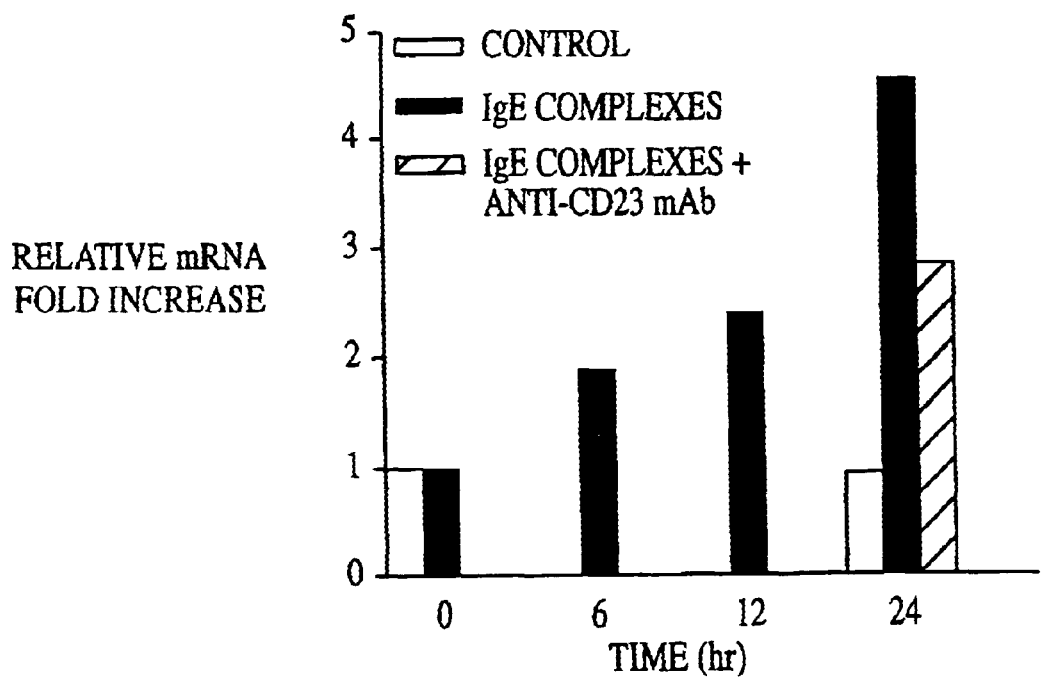

FIG. 8B is a graph depicting the corresponding time-dependent changes in the FcεRII/α-actin ratio, obtained from the data presented in FIG. 8A, expressed as fold increase above baseline (i.e., time 0) in control (open bars) and IgE immune complex-treated cells (filled bars).

FIG. 9A is a graph comprising two panels depicting a flow cytometric analysis of FcγRIII and FcεRII surface expression in rabbit ASM cells. Cells were treated for 24 hours with 10% control serum or 10% atopic asthmatic serum were stained with fluorescein isothiocyanate (FITC)-conjugated human monoclonal antibodies specific for the low-affinity FcγRIII (top panel) and FcεRII (CD23, lower panel) receptors. Activated B-cells (8.1.6) were used as a positive control for the CD23 receptor. The level of non-specific background staining was measured in both the control and atopic asthmatic serum-treated cells by staining with FITC-conjugated isotype control antibodies.

FIG. 9B is a graph comprising two panels depicting a flow cytometric analysis of FcγRIII and FcεRII surface expression in rabbit ASM cells. The cells were treated for 24 hours with 10% atopic/asthmatic serum and the cells were then stained with fluorescein isothiocyanate (FITC)-conjugated human monoclonal antibodies specific for the low-affinity FcγRIII (top panel) and FcεRII (CD23, lower panel) receptors. Activated B-cells (8.1.6) were used as a positive control for the CD23 receptor. The level of non-specific background staining was measured in both the control and atopic asthmatic serum-treated cells by staining with FITC-conjugated isotype control antibodies.

Figure 10A:
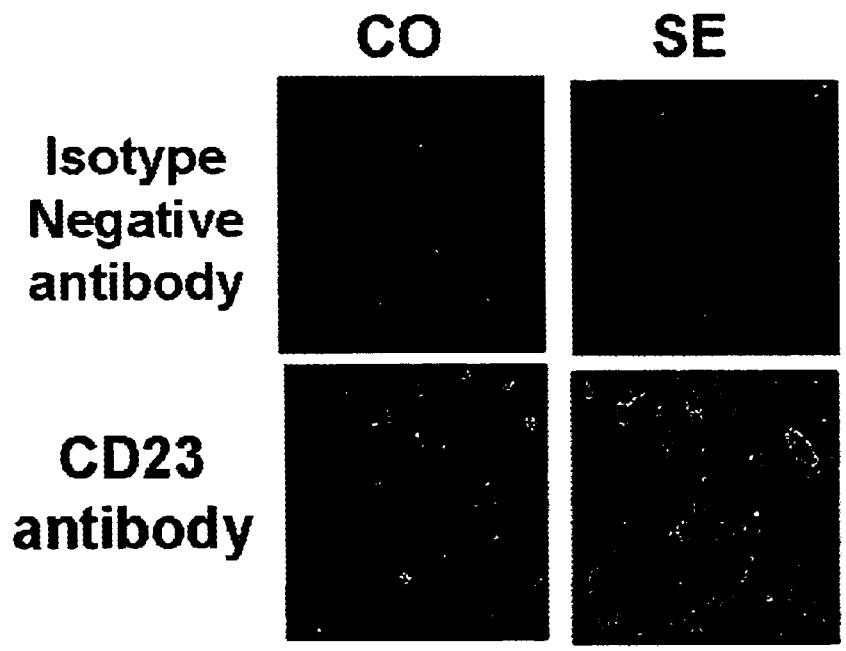

FIG. 10A is a series of images, comprising 4 panels, depicting immunofluorescence staining for CD23 surface receptor protein in control (CO) serum-treated (left panels) and atopic asthmatic serum (SE) sensitized (right panels) rabbit ASM cells (magnification×100). F(ab')$_2$-FITC conjugated fragments were used to detect the primary monoclonal anti-CD23 antibody. Isotype negative antibody was used as a negative control for nonspecific staining (upper panels).

Figure 10B:
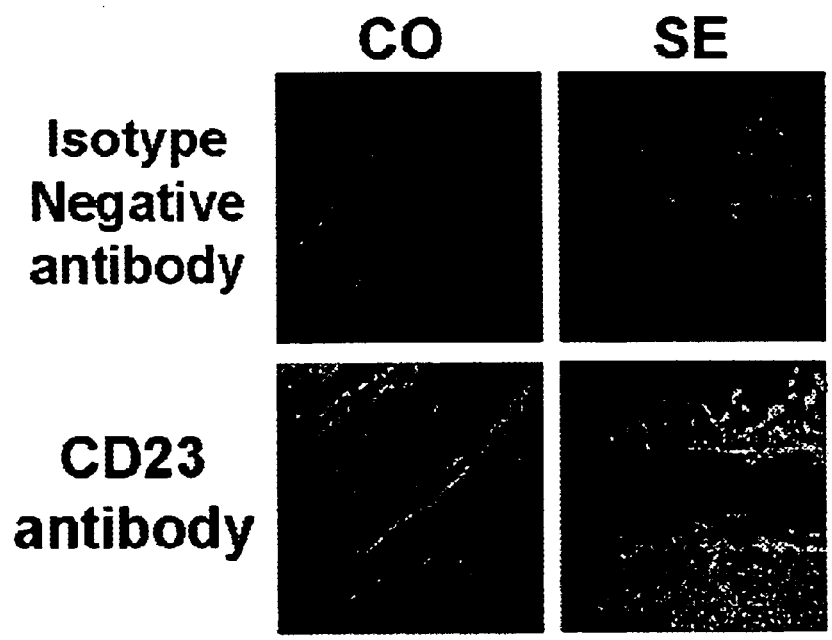

FIG. 10B is a series of images, comprising 4 panels, depicting immunofluorescence staining for CD23 surface receptor protein in control (CO) serum-treated (left panels) and atopic asthmatic serum (SE) sensitized (right panels) rabbit TSM tissue (magnification×50). F(ab')$_2$-FITC conjugated fragments were used to detect the primary monoclonal anti-CD23 antibody. Isotype negative antibody was used as a negative control for nonspecific staining (upper panels).

Figure 11:
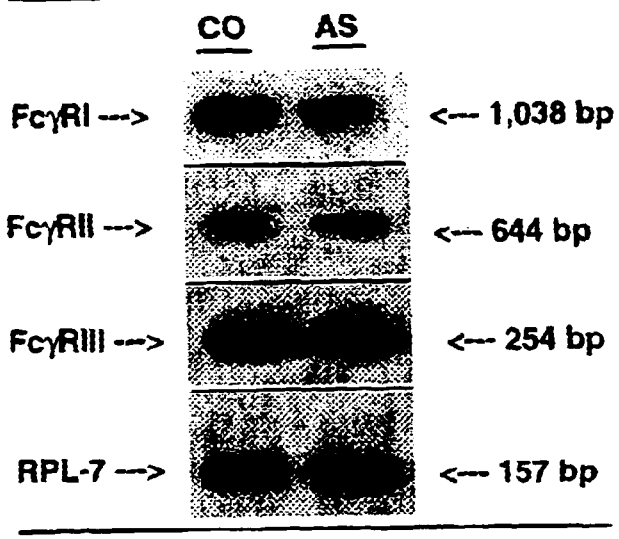

FIG. 11 is an image of a southern blot depicting the comparison of expression of FcγRI (1,038 bp), FcγRIIa,c (644 bp) and FcγRIII (254 bp) receptor mRNAs using RT-PCR in control (CO) and inherently asthmatic (AS) human ASM tissue to detect the RT-PCR amplification products. Expression of RPL7 (157 bp) was used as a positive control for loading. The northern blots were probed with human specific FcγRI, FcγRII, and FcγRIII $^{32}$P-labeled cDNA probes. Human ASM tissue expressed mRNA for both the high-affinity FcγRI and the low-affinity FcγRIIa,c and FcγRIII receptors, as determined by the expected sizes of the respective FcγRI, FcγRII and FcγRIII cDNA fragments, and there were no differences in the mRNA expression signals between control and asthmatic ASM. Data are representative of three separate experiments using ASM tissue isolated from patient #1. Comparable results were obtained using ASM tissue isolated from patient #2.

Figure 12:
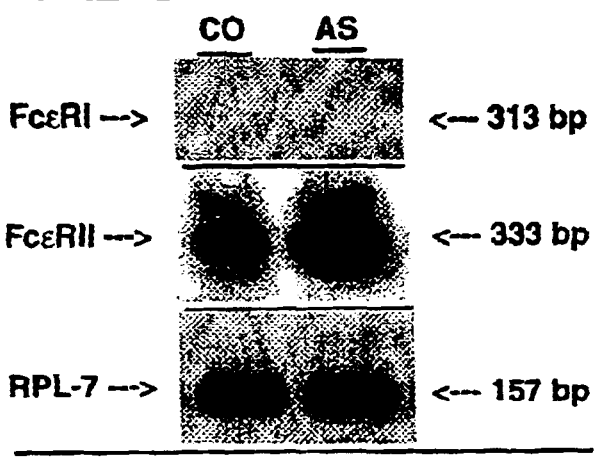

FIG. 12 is an image of a southern blot depicting the comparison of expression of FcεRI (313 bp) and FcεRII (333 bp) receptor mRNAs using RT-PCR in control (CO) and inherently asthmatic (AS) human ASM tissue. Expression of RPL7 (157 bp) was used to control for loading. The blots were probed with human specific FcεRI and FcεRII $^{32}$P-labeled cDNA probes. In contrast to undetectable expression of FcεRI, human ASM tissue expressed mRNA for the low-affinity FcεRII receptor, as determined by the expected size of its FcεRII cDNA fragment (CO), and the expression of the FcεRII was markedly increased in the inherently asthmatic human ASM (AS). Data are representative of three separate experiments using ASM tissue isolated from patient #1. Comparable results were obtained using ASM tissue isolated from patient #2.

FIG. 13 is an image of a representative Southern blot (n=4) prepared from paired human airway smooth muscle tissue samples incubated with control (CO) or atopic asthmatic (SE) serum for 24 hours. PCR products were amplified using human-specific FcεRII and RPL7 primers and probed with human specific 333-bp FcεRII and 157-bp RPL7 human $^{32}$P-labeled cDNA probes. The data disclosed demonstrate a marked induction of FcεRII expression in the atopic asthmatic serum-sensitized sample (SE).

FIG. 14A is an image of a Southern blot comparing the expression of FcεRII mRNA in human airway smooth muscle tissue following 24 hours of treatment with either control (CO) or atopic asthmatic serum in the absence (SE) and presence (SE+) of anti-CD23 mAb. The data disclosed herein demonstrate that anti-CD23 mAb significantly attenuated the induction of FcεRII mRNA expression in the atopic asthmatic-serum sensitized ASM. Data are representative of four separate experiments.

FIG. 14B is an image of a Southern blot depicting the comparison of FcεRII mRNA expression in human ASM treated for 24 hours with vehicle alone (CO) or maximal effective concentrations of IgE alone or IgE immune complexes (IgE cx). The products of the RT-PCR reactions using human-specific primers for the FcεRII receptor mRNA are shown. Expression of RPL7 was used to control for gel loading. The blots were probed with the $^{32}$P-labeled human-specific FcεRII and RPL7 cDNA probes. The data disclosed herein is comparable to that presented in FIG. 14A in that treatment of human ASM with IgE immune complexes also significantly induced enhanced mRNA expression of FcεRII, whereas IgE alone had lesser effect. Data are representative of four separate experiments.

Figure 15:
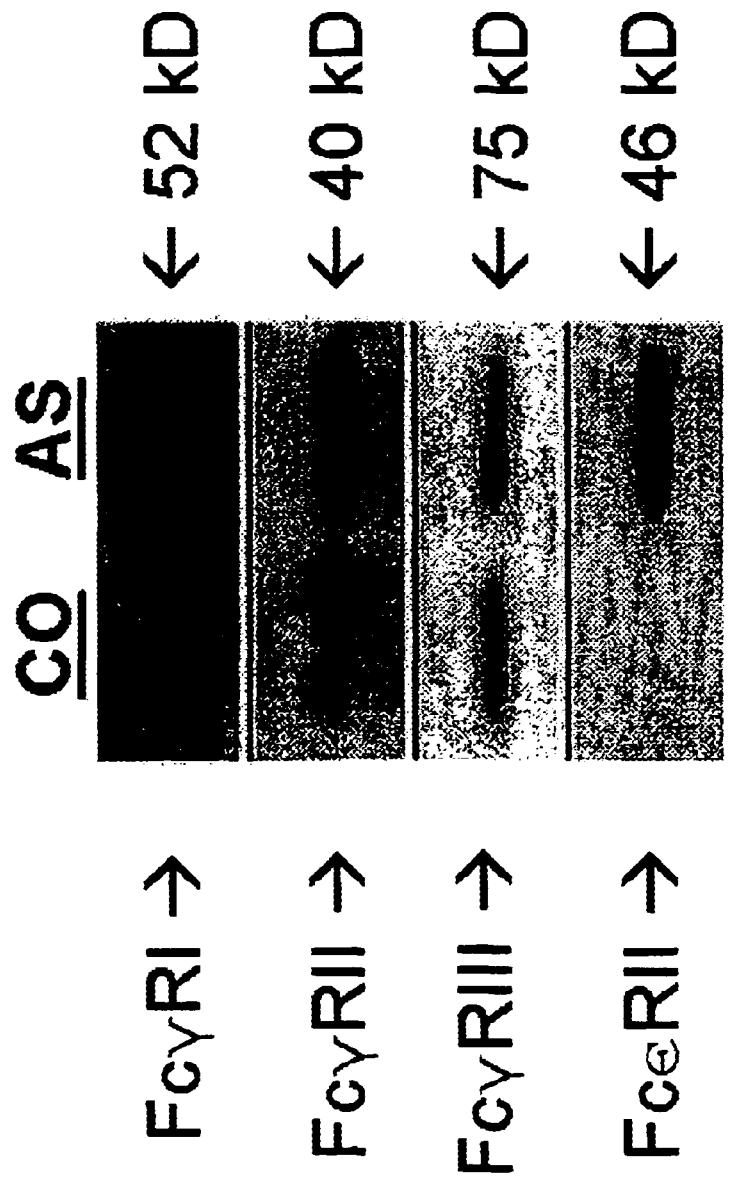

FIG. 15 is an image of a Western blot depicting FcγRI (approximately 52 kD), FcγRII (approximately 40 kD), FcγRIII (approximately 75 kD), and FcεRII (approximately 46 kD) expression in membrane homogenates from human control (CO) and inherently asthmatic (AS) human ASM tissue. Fifty μg of membrane protein was loaded in each gel lane. In contrast to unaltered FcγRI, FcγRII and FcγRIII expression, relative to control ASM, expression of FcεRII protein was significantly enhanced in the inherently asthmatic ASM. Data are representative of three separate experiments using ASM tissue isolated from patient #1. Comparable results were obtained using ASM tissue isolated from patient #2.

Figure 16A:
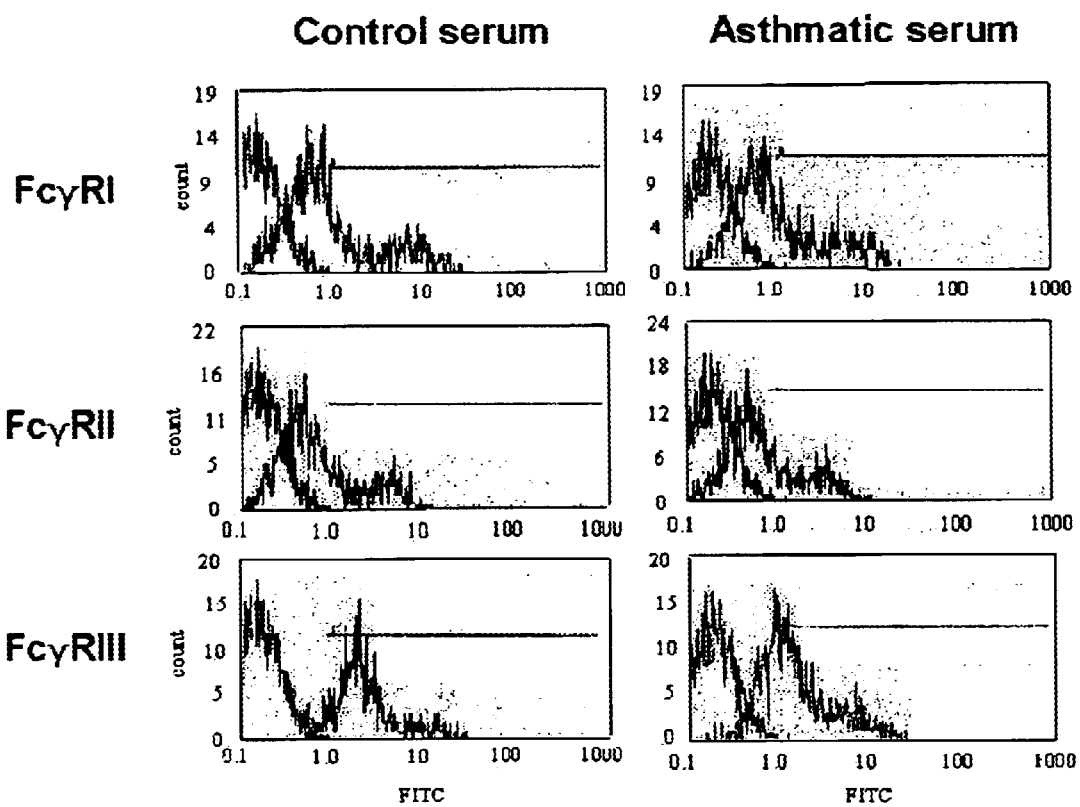

FIG. 16A is a graph, comprising six panels; depicting representative flow cytometric analysis (n=3) of FcγRI, FcγRII and FcγRIII cell surface protein expression in human ASM cells treated for 24 hours with human control serum (left panels) or human atopic asthmatic serum (right panel). The ASM cells were stained with mouse anti-human monoclonal antibodies specific for the individual FcγRI, FcγRII and FcγRIII. The levels of non-specific background staining were measured for each monoclonal antibody by staining with isotype control IgG antibody (left histogram in each panel). Goat anti-mouse FITC-conjugated secondary antibody was used for detection of the signals. Relative to cells exposed to control serum, there was significantly induced enhanced cell surface staining for FcεRII in cells that were exposed to atopic asthmatic serum. In contrast, atopic asthmatic serum had no appreciable effect on FcγRI, FcγRII or FcγRIII expression.

Figure 16B:
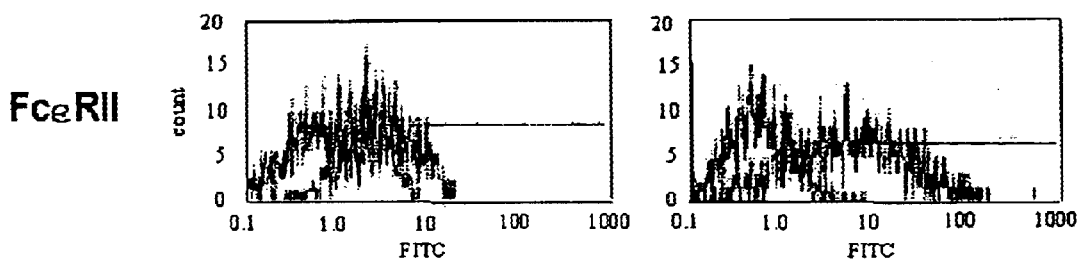

FIG. 16B is a graph, comprising two panels, depicting representative flow cytometric analysis (n=3) of FcεRII cell surface protein expression in human ASM cells treated for 24 hours with human control serum (left panel) human atopic asthmatic serum (right panel). The ASM cells were stained with mouse anti-human monoclonal antibodies specific for the individual FcεRII receptor. The level of non-specific background staining was measured by staining with isotype control IgG antibody (left histogram in each panel). Goat anti-mouse FITC-conjugated secondary antibody was used for detection of the signals. Relative to cells exposed to control serum, there was significantly induced enhanced cell surface staining for FcεRII in cells that were exposed to atopic asthmatic serum. In contrast, atopic asthmatic serum had no appreciable effect on FcγRI, FcγRII or FcγRIII expression (FIG. 16A).

Figure 17:
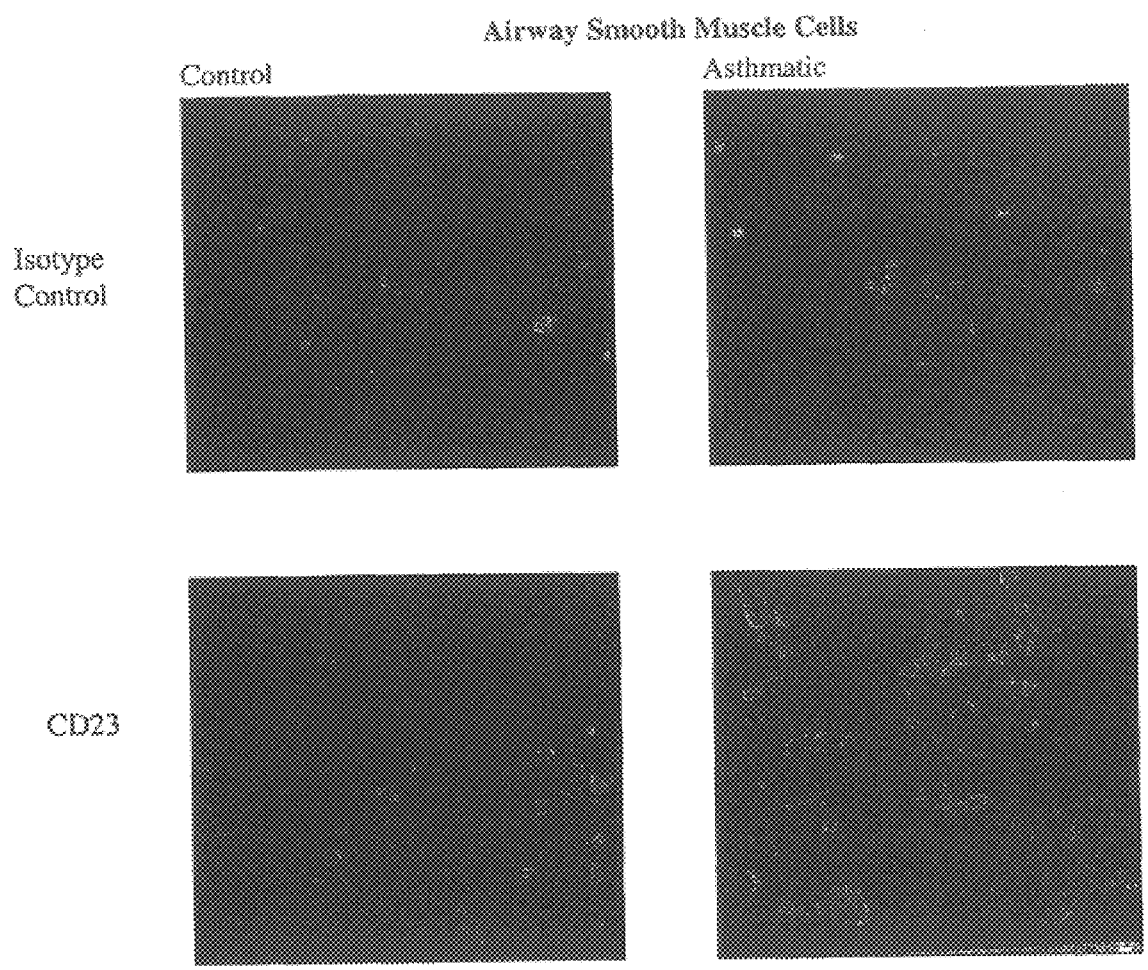

FIG. 17 is an image, comprising four panels, depicting representative immunofluorescence staining (n=4) for CD23 surface receptor protein in control serum-treated (left panels) and atopic asthmatic serum sensitized (right panels) ASM cells (magnification×100). F(ab')2-FITC conjugated fragments were used to detect the primary monoclonal anti-CD23 antibody. Isotype negative control antibody was used to control for nonspecific staining (upper panels). The data disclosed herein demonstrate that FcεRII (CD23) receptor staining is significantly enhanced in ASM cells that were treated with atopic asthmatic serum.

Figure 18A:
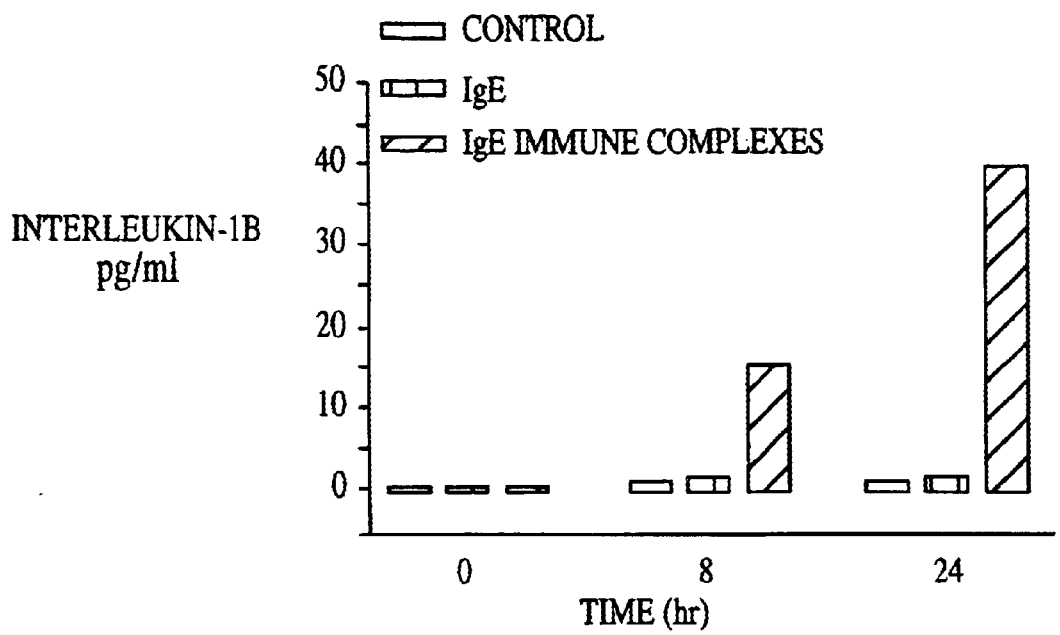

FIG. 18A is a graph comparing the levels of human IL-1β protein released into the culture media of ASM tissues following 0, 8 and 24 hours exposure to SFM alone (open bar), IgE (hatched bar) or IgE immune complexes (filled bar). The data disclosed herein and in FIG. 18B demonstrate that human ASM tissue exposed to IgE immune complexes or to atopic asthmatic serum released significantly increased levels of IL-1β protein into the tissue culture medium, whereas treatment with serum-free medium, human control serum, or IgE alone had no appreciable effect. Moreover, this effect of the atopic asthmatic serum was largely prevented by pretreatment with an anti-CD23 mAb. Data are representative of three separate experiments.

Figure 18B:
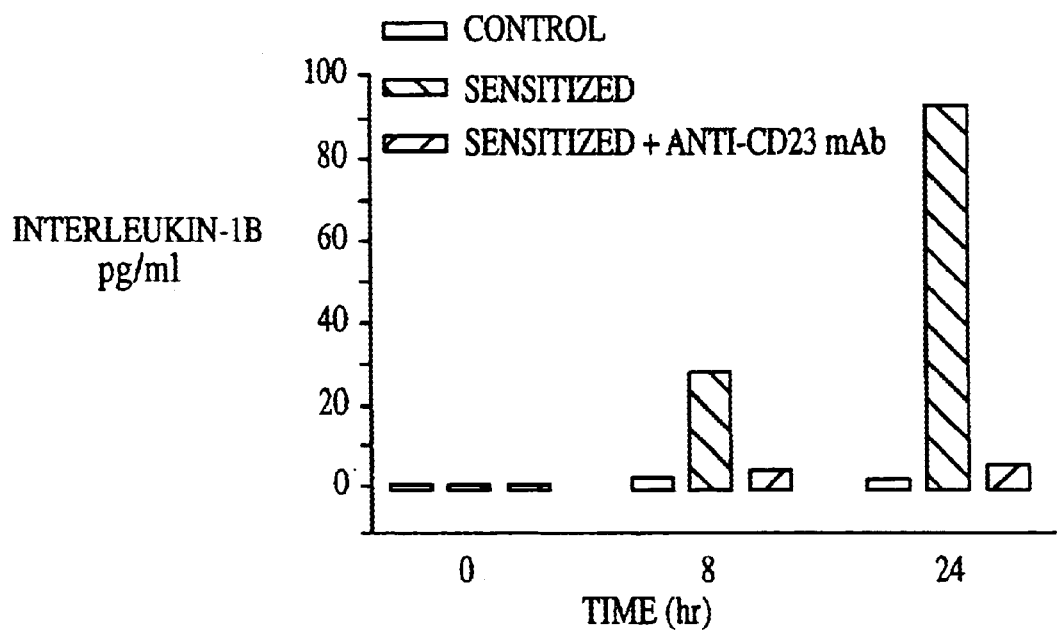

FIG. 18B is a graph comparing the levels of human IL-1β protein released into the culture media of ASM tissues following 0, 8 and 24 hours exposure to human control serum (open bar), or human atopic asthmatic serum in the absence (hatched bar) and presence (filled bar) of anti-CD23 mAb. The data disclosed herein and in FIG. 18A demonstrate that human ASM tissue exposed to IgE immune complexes or to atopic asthmatic serum released significantly increased levels of IL-1β protein into the tissue culture medium, whereas treatment with serum-free medium, human control serum, or IgE alone had no appreciable effect. Moreover, this effect of the atopic asthmatic serum was largely prevented by pretreatment with an anti-CD23 mAb. Data are representative of three separate experiments.

DETAILED DESCRIPTION OF THE INVENTION

The invention relates to the discovery of the expression of an Fc receptor protein on airway smooth muscle cells, which expression plays a significant role in the development of the asthmatic state in an individual having asthma. While expression of the receptor of the invention on other cell types is known, expression of the receptor on airway smooth muscle cells has been heretofore unknown.

The receptor of the invention is a receptor for IgE termed FcεRII or CD23. This receptor is a low affinity receptor for IgE which has been observed to be expressed in an inducible form on monocytes and lung alveolar macrophages (Williams et al., 1992, J. Immunol. 149:2823–2829; Joseph et al., 1983, J. Clin. Invest. 71:221–230), as well as on circulating B lymphocytes (Gagro et al., 1993, Int. Arch. Allergy Immunol. 101:203–208; Rabatic et al., 1993, Exp. Immunol. 94:337–340), isolated from atopic asthmatic individuals. However, until the present discovery, the expression of this receptor on airway smooth muscle cells has not been known.

In addition to the discovery of the expression of the FcεRII receptor on airway smooth muscle cells, the present invention includes the discovery that antibodies directed against this receptor block the induction of the asthmatic state. Thus, the invention includes a method of preventing induction of the asthmatic state in a mammal, which method comprises administering to the mammal a pharmaceutically effective amount of an anti-FcεRII receptor ligand. The ligand binds to the FcεRII receptor protein, thereby inhibiting binding of IgE to the FcεRII receptor protein. Inhibition of binding of IgE to the FcεRII receptor protein serves to prevent induction of the asthmatic state.

The invention also includes a method of treating asthma in a mammal, which method comprises administering to the mammal a pharmaceutically effective amount of an anti-FcεRII receptor ligand. The ligand binds to the FcεRII receptor protein, thereby inhibiting binding of IgE to the FcεRII receptor protein. Inhibition of binding of IgE to the FcεRII receptor protein serves to diminish or ablate the asthmatic state in the mammal thereby treating asthma in the mammal. Preferably, the mammal is a human.

There are two types of FcεRII receptor proteins, FcεRIIa and FcεRIIb, which differ in only six to seven N-terminal amino acids. Both receptor proteins are derived from the same gene through the use of different promoters which control expression of separate first exons of the protein, which exons are spliced to a common mRNA sequence (Delespease et al., 1992, Immunol. Rev. 125:78–97). The invention should be construed to include both receptor proteins.

By the term "asthmatic state" as used herein, is meant the proasthmatic phenotype which is observed in airway smooth muscle cells. This phenotype is characterized by increased contraction and decreased relaxation of the airway tissue when it has been exposed to high IgE-containing atopic asthmatic serum or exogenous IgE, compared with airway tissue which has not been exposed to IgE.

By the term "treating asthma" is meant curing asthma, causing the symptoms of asthma to diminish, ablating or otherwise alleviating the disease.

The invention should be construed to include any ligand that is currently either known or is heretofore unknown, which when bound to an FcεRII receptor protein on an airway smooth muscle cell of a mammal serves to alleviate an asthmatic state in the mammal.

By the term "ligand" as used herein, is meant any natural or synthetic composition or compound which is capable of specifically binding to its cognate receptor protein, and when so bound, prevents binding of IgE to the cognate receptor protein, such that an asthmatic state is prevented or diminished. By way of example, an antibody which specifically binds to an FcεRII receptor protein on an airway smooth muscle cell and inhibits binding of IgE thereto, is termed an "anti-FcεRII receptor protein ligand." In this context, the FcεRII receptor protein is the "cognate receptor protein" for the ligand.

By the term "anti-FcεRII receptor protein ligand" as used herein, is meant any natural or synthetic composition or compound which is capable of binding to an FcεRII receptor protein on an airway smooth muscle cell, which binding prevents binding of IgE to the cognate FcεRII receptor protein.

Preferably, the anti-FcεRII receptor protein ligand is an antibody.

The invention should not be construed to be limited to the specific ligands and respective cognate receptor proteins disclosed in the Examples presented herein. Rather, the invention should be construed to include any presently known or heretofore unknown ligands which have the effect of inhibiting binding of an IgE molecule to an FcεRII receptor protein on an airway smooth muscle cell. It is a simple matter, upon reading the present disclosure, to use the IgE binding inhibition assays described in the Examples to identify additional ligands which bind to an FcεRII receptor protein and inhibit the binding of IgE thereto. Thus, while preferred ligands for use in the methods of the invention are antibodies directed to an FcεRII receptor protein, yet other useful ligands may be identified using the protocols described herein. The most preferred ligand for use in the methods of the invention is an antibody which is an anti-FcεRII receptor protein ligand.

To identify a ligand capable of binding to an FcεRII receptor protein expressed on an airway smooth muscle cell and inhibiting binding of IgE thereto, a mixture comprising a population of cells, for example, airway smooth muscle cells which express an FcεRII receptor protein, and IgE is incubated in the presence or absence of a test ligand. Binding of IgE to the cells is then assessed. The level of binding of IgE to cells incubated in the presence of the test compound is compared with the level of binding of IgE to cells in the absence of the test compound. A lower level of IgE binding to cells in the presence of the test compound compared with the level of binding of IgE to the cells in the absence of the test compound is an indication that the test compound is an anti-FcεRII receptor protein ligand. Additional assays which definitively establish that the test compound is capable of binding to an FcεRII receptor protein and preventing the binding of IgE thereto, may then be conducted following the protocols provided herein in the Examples section.

The ligand for use in the method of the invention may be any natural or synthetic composition or compound which when bound to its cognate receptor protein, effects the inhibition of binding of IgE to the cognate receptor protein. Thus, the ligand may be a protein, a peptide or a small molecule. The ligand may be administered to a cell as is, that is, as an isolated protein, an isolated peptide, a small molecule, or it may be administered to the cell in the form of an isolated nucleic acid sequence encoding the ligand.

By the term "isolated nucleic acid", as used herein, refers to a nucleic acid sequence, a DNA or an RNA or fragment thereof which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequences.

In other related aspects, the invention includes vectors which contain such isolated nucleic acid and which are preferably capable of directing expression of the protein encoded by the nucleic acid in a vector-containing cell; and cells containing such vectors, either eukaryotic cells or prokaryotic cells, preferably eukaryotic cells.

The isolated nucleic acid of the invention should be construed to include an RNA or a DNA sequence encoding a ligand of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

By the terms "isolated peptide" or "isolated protein," as used herein, is meant a peptide or protein which has been substantially separated from the components, e.g,. DNA, RNA, other proteins and peptides, carbohydrates and lipids, which naturally accompany the protein or peptide in the cell. The terms isolated peptide and protein may be construed to include a peptide or protein which is expressed and/or secreted from a cell comprising an isolated nucleic acid.

The present invention also provides for analogs of proteins or peptides which comprise a ligand as defined herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g, D-amino acids or non-naturally occurring synthetic amino acids. The peptides of the invention are not limited to products of any of the specific exemplary processes listed herein.

Desirable isolated protein or isolated peptide ligands include antibodies which bind to the desired cognate receptor protein. The antibody may be any type of antibody including, but not limited to, a polyclonal antibody, a monoclonal antibody, a synthetic antibody, a chimeric antibody, a humanized antibody, and the like. Other anti-FcεRII receptor protein ligands include proteins which are not antibodies.

Antibody technology is described in Harlow et al. (1988, In: Antibodies, A Laboratory Manual, Cold Spring Harbor, N.Y.). Polyclonal antibodies directed against an FcεRII receptor protein may be made by immunizing any suitable animal and obtaining immune serum from the animal at selected intervals following immunization.

Monoclonal antibodies directed against full length or peptide fragments of an FcεRII receptor protein may be prepared using any well known monoclonal antibody preparation procedures, such as those described, for example, in Harlow et al. (supra). Quantities of the desired peptide may also be synthesized using chemical synthesis technology. Alternatively, DNA encoding the desired peptide may be cloned and expressed from an appropriate promoter/regulatory sequence in cells which are suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125–168) and the references cited therein. Further, the antibody may be "humanized" using the technology described in Wright et al., (supra) and in the references cited therein.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning. A Laboratory Manual, Cold Spring Harbor, N.Y.) and in Ausubel et al. (1993, Current Protocols in Molecular Biology, Green & Wiley, New York).

Bacteriophage which encode the desired antibody, may be engineered such that the protein is displayed on the surface thereof in such a manner that it is available for binding to its corresponding binding protein, e.g. the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., supra.

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA.encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al., 1995, J. Mol. Biol. 248:97–105).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The invention thus includes an isolated DNA encoding an anti-FcεRII receptor protein ligand or DNA encoding a portion of the ligand, which when the ligand is, for example, an antibody, the antibody is itself specific for its cognate receptor protein, or for fragments thereof.

To isolate DNA encoding an antibody, for example, DNA is extracted from antibody expressing phage obtained as described herein. Such extraction techniques are well known in the art and are described, for example, in Sambrook et al. (supra) and in Ausubel et al. (supra).

By the term "scFv/phage" are used herein, is meant a phage particle which expresses the Fv portion of an antibody as a single chain.

The invention should be construed to include other anti-FcεRII receptor protein-binding ligands which are either known or are heretofore unknown, which are, or will be designed to bind to an FcεRII receptor protein and which are useful for treating or preventing the asthmatic state in an individual.

Another form of ligand includes a nucleic acid sequence which encodes the anti-FcεRII receptor protein ligand and which is associated with promoter/regulatory sequences which can direct expression of the anti-FcεRII receptor protein ligand in vivo. For a discussion of this technology, see, for example, Cohen (1993, Science 259:1691–1692), Fynan et al. (1993, Proc. Natl. Acad. Sci. U.S.A. 90:11478–11482) and Wolff et al. (1991, Biotechniques 11:474–485) which describe the use of naked DNA as a therapeutic agent. For example, a plasmid containing suitable promoter/regulatory sequences operably linked to a DNA sequence encoding an anti-FcεRII receptor protein ligand, may be directly administered to a patient using the technology described in the aforementioned references.

As used herein, the term "promoter/regulatory sequence" means a DNA sequence which is required for tissue-specific, organ specific, or other specific (such as inducible, etc) expression of a nucleic acid operably linked to the promoter/regulatory sequence. In some instances, this sequence may be the core promoter sequence and in other instances, this sequence may also include an enhancer sequence and other regulatory elements which are required for expression of the gene in the desired specific manner.

By describing two nucleic acid sequences as "operably linked" as used herein, is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

Alternatively, the promoter/regulatory sequence operably linked to DNA encoding the anti-FcεRII receptor protein ligand may be contained within a vector, which vector is administered to the patient.

By the term "vector" as used herein, is meant any plasmid or virus encoding an exogenous nucleic acid. The term should also be construed to include non-plasmid and non-viral compounds which facilitate transfer of nucleic acid into cells, such as, for example, polylysine compounds and the like. The vector may be a viral vector which is suitable as a delivery vehicle for delivery of the anti-FcεRII receptor protein ligand DNA to the patient, or the vector may be a non-viral vector which is suitable for the same purpose. Examples of viral and non-viral vectors for delivery of DNA to cells and tissues are well known in the art and are described, for example, in (Ma et al., 1997, Proc. Natl. Acad. Sci. U.S.A. 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. W)94/23744, published Oct. 27, 1994). Examples of non-viral vectors include, but are not limited to, liposomes, polyamine derivatives of DNA, and the like.

The identity, selection and means for obtaining a desired anti-FcεRII receptor protein ligand useful for treatment or prevention of asthma may be performed by the skilled artisan using conventional technology when in possession of the present invention. For example, as described in the Examples presented herein, there are a variety of anti-FcεRII monoclonal antibodies which are available that are likely anti-FcεRII receptor protein ligands suitable for use in the methods of the invention.

Other anti-FcεRII receptor protein ligands may include, but are not limited to, isolated proteins and isolated polypeptides and isolated nucleic acid sequences encoding the same. Isolated proteins and peptides having anti-FcεRII receptor protein ligand activity and isolated nucleic acids encoding the same, may be chemically synthesized by conventional methods known in the art, or they may be purchased for a commercial source if available. In one embodiment of the invention, the anti-FcεRII receptor protein ligand, being a protein, a peptide or a nucleic acid, may be produced using recombinant techniques in vitro in sufficiently large quantities for use in a therapeutic composition for use in treating or preventing asthma. In addition, a recombinant virus vector comprising DNA encoding the desired anti-FcεRII receptor protein ligand may be prepared using conventional recombinant DNA technology procedures.

The ligand useful in the methods of the invention may be a small molecule, a non-peptide, a peptidometic, and the like, which ligand binds to an FcεRII receptor protein thereby inhibiting binding of IgE to the receptor protein. Once in possession of the present invention, it is within the skill of the ordinary artisan to identify the contact points between the ligand and the cognate receptor protein, which contact points are essential for binding of these molecules together to inhibit binding of IgE to the receptor protein. Thus, it is also within the skill of the artisan to design specific peptidometics which bind to FcεRII receptor protein. The invention should be construed to include such peptidometics. The technology of the development of peptidometics is described, for example, in PCT/US93/01201 and U.S. Pat. No. 5,334,702.

The anti-FcεRII receptor protein ligand of the invention may be formulated in a pharmaceutical composition which is suitable for administration of the ligand to a human patient. It will be appreciated that the precise formulation and dosage amounts will vary depending upon any number of factors, including, but not limited to, the type and severity of the disease to be treated, the route of administration, the age and overall health of the individual, the nature of the ligand, etc. However, the preparation of a pharmaceutically acceptable composition having an appropriate pH, isotonicity, stability and other characteristics is within the skill of the art. Pharmaceutical compositions are described in the art, for example, in Remington's Pharmaceutical Sciences (Genaro ed., 1985, Mack Publishing Co., Easton, Pa.).

As used herein, the term "pharmaceutically-acceptable carrier" means a chemical composition with which an appropriate anti-FcεRII receptor protein ligand, may be combined and which, following the combination, can be used to administer the ligand to a patient.

The amount of the anti-FcεRII receptor protein ligand composition administered, whether it is administered as protein or as nucleic acid, is sufficient to prevent, diminish or alleviate the asthmatic state. The pharmaceutical compositions useful for practicing the invention may be administered to deliver a dose of between about 1 ng/kg and about 100 mg/kg of patient body weight. Suitable amounts of the anti-FcεRII receptor protein ligand for administration include doses which are high enough to have the desired effect without concomitant adverse effects. When the anti-FcεRII receptor protein ligand is a protein or peptide, a preferred dosage range is from about 10 to about 1000 μg of protein or peptide per kg of patient body weight. When the anti-FcεRII receptor protein ligand is administered in the form of DNA encoding the same contained within a recombinant virus vector, a dosage of between about $10^2$ and about $10^{11}$ plaque forming units of virus per kg of patient body weight may be used. When naked DNA encoding the anti-FcεRII receptor protein ligand is to be administered as the pharmaceutical composition, a dosage of between about 10 μg about several mg of DNA per kg of patient body weight may be used.

In the practice of the methods of the invention, a composition containing an anti-FcεRII receptor protein ligand is administered to a patient in a sufficient amount to prevent, diminish or alleviate an asthmatic state in the individual. Patients to be treated include children and adults who have atopic (allergic) asthma. This constitutes the vast majority of asthmatic individuals.

The frequency of administration of an anti-FcεRII receptor protein ligand to a patient will also vary depending on several factors including, but not limited to, the type and severity of the asthma to be treated, the route of administration, the age and overall health of the individual, the nature of the anti-FcεRII receptor protein ligand, etc. It is contemplated that the frequency of administration of the anti-FcεRII receptor protein ligand to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate anti-FcεRII receptor protein ligand, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate anti-FcεRII receptor protein ligand to a patient according to the methods of the invention.

Preferably, the composition of the invention is administered to the human by a lung inhalation route, i.e., via a nebulizer or other lung inhalation device.

An anti-FcεRII receptor protein ligand may be administered in conjunction with other compounds which are used to treat asthma. Such compounds include, but are not limited to, corticosteroids, sodium cromolyn, methylxanthnies, leukotriene modifiers), anti-cholinergic agents, and rapid relief medications that counteract bronchospasm, e.g., primarily beta-adrenergic agents. The choice of which additional compound to administer will vary depending upon any number of the same types of factors that govern the selection of dosage and administration frequency of the anti-FcεRII receptor protein ligand. Selection of these types of compounds for use in conjunction with an anti-FcεRII receptor protein ligand for practice of the method of the invention is well within the skill of those in the art.

The invention also includes a method of regulating production of interleukin-1β in a cell. The method comprises contacting a cell with an anti-FcεRII receptor protein ligand such that the IgE/FcεRII receptor protein interaction is inhibited. In one embodiment, the IgE/FcεRII receptor protein interaction mediates elaboration of IL-1β by rabbit and human ASM cells and tissue. One skilled in the art would appreciate based on the disclosure provided herein, that inhibition of this interaction inhibits production of IL-1β by the cells.

Further, the present invention should not be construed to be limited to rabbit or to human ASM. Rather, the invention should be construed to encompass other mammals such as dogs, cats, sheep, goats, cattle, and the like, as well as non-domestic and/or rare animals.

The invention will be further described by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Expression of Low Affinity IgE Receptor, FcεRII, in Airway Smooth Muscle (ASM)

The experiments presented were designed to examine whether ASM cells have the capacity to intrinsically express Fc receptors. The experiments were also designed to examine whether the expression and activation of these Fc receptors is altered in the atopic asthmatic sensitized state, which alteration may contribute to changes in agonist responsiveness of the ASM tissue. The results demonstrate that a) enhanced constrictor and attenuated relaxation responsiveness induced in ASM passively sensitized with human atopic asthmatic serum are prevented by depleting the sensitizing serum of its immune complexes or by blockade of FcεRII activation with an anti-CD23 blocking antibody; b) exposure of ASM cells and tissue to atopic asthmatic serum induces autologously upregulated mRNA and cell surface expression of FcεRII receptors by the ASM and; c) the latter induced upregulated expression of the FcεRII receptor in the atopic sensitized state is ablated by an anti-CD23 blocking antibody. Taken together, these observations provide new evidence that airway smooth muscle cells intrinsically express Fc receptors and that the induced altered responsiveness of atopic asthmatic sensitized airway smooth muscle is largely attributed to its autologously upregulated expression and activation of the FcεRII receptor subtype. Notwithstanding the well-established contribution of airway infiltrating inflammatory cells in the pathogenesis of atopic asthma (Beasley et al., 1989, Am. Rev. Respir. Dis. 139:806–817; Litchfield et al., 1992, J. Asthma 29:181–191; Barnes et al., 1988, Pharmacol. Rev. 40:49–84), the present novel findings identify a critical role for the airway smooth muscle itself in autologously regulating IgE/CD23-coupled changes in airway reactivity which characterize the asthmatic state. The data may be summarized as follows.

To elucidate the role of immunoglobulin (Ig) E-dependent mechanisms in inducing altered airway responsiveness in the atopic asthmatic state, the expression and actions of Fc receptor activation were examined in isolated rabbit tracheal smooth muscle (TSM) tissue and cultured cells passively sensitized with sera from atopic asthmatic patients or nonatopic/nonasthmatic (control) subjects. Relative to control tissues, the atopic asthmatic-sensitized TSM exhibited significantly increased maximal isometric contractility to acetylcholine (p<0.01) and attenuated maximal relaxation responses and sensitivity (i.e., −log $ED_{50}$) to isoproterenol (p<0.005). These changes in agonist responsiveness in atopic sensitized TSM were ablated by pretreating the tissues with a monoclonal blocking antibody (MAb) to the low affinity receptor for IgE, FcεRII (i.e., CD23) or by depleting the sensitizing serum of its immune complexes. Moreover, in complimentary experiments, exogenous administration of IgE immune complexes to naive TSM produced changes in agonist responsiveness which were qualitatively similar to those obtained in the atopic asthmatic sensitized state. Additional experiments established that, in contrast to their respective controls, atopic asthmatic serum-sensitized human and rabbit TSM tissue and cultured cells exhibited markedly induced mRNA and cell surface expression of FcεRII, whereas constitutive expression of the IgG receptor subtype, FcγRIII, was unaltered. Moreover, the upregulated mRNA expression of FcεRII observed following exposure of TSM to atopic asthmatic serum or to exogenously administered IgE immune complexes was significantly inhibited by pretreating the tissues or cells with anti-CD23 MAb. Collectively, these data provide new evidence demonstrating that the altered agonist responsiveness in atopic asthmatic sensitized airway smooth muscle is largely attributed to IgE-mediated induction of the autologous expression and activation of FcεRII receptors in the airway smooth muscle itself:

The Materials and Methods used in the experiments presented in this Example are now described.

Animals

Thirty four adult New Zealand White rabbits were used in the present study which was approved by the Biosafety and Animal Research Committee of the Joseph Stokes Research Institute at The Children's Hospital of Philadelphia. The animals exhibited no signs of respiratory disease for several weeks before the study.

Preparation and Sensitization of Airway Smooth Muscle Tissue

Rabbits were anesthetized with xylazine (10 mg/kg) and ketarnine (50 mg/kg) and were subsequently sacrificed using an overdose of pentobarbital (130 mg/kg). The tracheae of the rabbits were removed via open thoracotomy, the tracheae were cleared of loose connective tissue and were divided into eight ring segments of 6–8 mm length. Each segment referred to herein as a tracheal smooth muscle (TSM) segment was incubated for 24 hours at room temperature in either of the following: 1) human serum containing immunoglobulin (Ig) E at greater than 1000 IU/ml which was obtained from allergic patients having moderate to severe asthma and a 4–5/6+radioallergosorbent test (RAST) positive (having a specific IgE concentration of more than 17.5 Phadebas RAST units (PRU)/ml) to *Dermatophagoides pteronyssimus, Dermatophagoides farinae* and ragweed, and a positive skin test to these antigens; or 2) human serum obtained from non-atopic, non-asthmatic individuals having normal serum IgE levels (i.e., <70 IU/ml) and negative skin test reactivity to *Dermatophagoides pteronyssimus, Dermatophagoides farinae* and ragweed (Hakonarson et al. 1995, Am. J. Physiol. (Lung Cell Mol. Physiol.) 269:L645-L652).

In parallel experiments, TSM segments were incubated in either control serum or in atopic asthmatic serum that was: a) depleted of its immunoglobulin complexes by pretreatment with sepharose Staphylococcus protein A as described (Kessler, 1975, J. Immunol. 1 15:161.7–1624); b) co-incubated with an anti-CD23 (40 µg/ml) monoclonal blocking antibody; or c) with an anti-CD 16 (2 µg/ml) monoclonal blocking antibody. The TSM segments were treated with their respective anti-CD23 or anti-CD16 antibodies in Dulbecco's modified Eagle's medium for 1 hour prior to exposure to the atopic asthmatic serum.

In extended experiments, paired TSM segments were incubated for 24 hours in Dulbecco's modified Eagle's medium, as previously described (Hakonarson et al., 1996, J. Clin. Invest. 97:2593–2600), containing either: a) human IgE (final bath concentration (FBC): 15 µg/ml); or b) human IgE-goat-anti-human IgE immune complexes (FBC: 15:5 µg/ml of IgE/anti-IgE in the final organ bath mixture). Tissues incubated in medium alone served as controls. The concentrations of immune complexes used for the TSM incubations were based on the results obtained in pilot studies which were designed to determine the concentration and ratio of immune complexes that induced the greatest acute contractile effect in isolated sensitized TSM segments. The serum was aerated with a continuous supplemental $O_2$ mixture (95% $O_2$/5% $CO_2$) during the incubation phase.

In comparable experiments, the passive sensitization protocol described above was also conducted on human tracheal smooth muscle which was isolated 1 hour post-mortem from a 53 year-old male who died from a central nervous system complication of immune thrombocytopenia and had no evidence of lung disease. The passive sensitization protocol was also conducted on a surgically resected human bronchial smooth muscle segment.obtained from a 72 year-old female with peripheral lung carcinoma. Microscopically normal airway smooth muscle was carefully cleaned of loose connective tissue and epithelium and divided into 4–5 mm long strips. As above, each alternate adjacent strip was incubated in either control or atopic asthmatic serum in the absence or presence of an anti-CD23 antibody and was subsequently examined for Fc receptor expression (see below).

Preparation and sensitization of airway smooth muscle cells Airway smooth muscle (ASM) cells were cultured according to described protocols. These cells have been characterized in detail with respect to their distinguishing morphological, histological, and immunological features. The cell isolation and subcultivation procedures, and the characterization of the cells is described in Noveral et al. (1992, Am. J. Physiol. (Lung Cell. Mol. Physiol.) 263:L555-L56 1). Briefly, ASM cells were isolated from epithelium-denuded trachealis muscle obtained from adult New Zealand White rabbits. Following digestion in F-12 culture medium containing 30 mg/ml protease, 55 mg/ml type IV collagenase, and 100 mg/ml trypsin inhibitor, the dissociated cells were centrifuged and resuspended in F-12 containing 10% fetal bovine serum (FBS) and 100 µg/ml of gentamicin sulfate. The cells were then inoculated in 100 mm tissue culture dishes and, after 4 weeks, the cells had sufficiently proliferated to permit routine subcultivations. At weekly intervals, the subcultivated cells were suspended and then inoculated at a density of $1 \times 10^4$ cells/cm$^2$ in 75 cm$^2$ tissue culture flasks containing F-12 supplemented with 20% FBS and were then incubated at 37° C. in a humidified atmosphere of 5% $CO_2$/95% air. Routine tests for mycoplasma contamination were negative. For the sensitization protocol, cells initially seeded at $1 \times 10^4$ cells/cm$^2$ in 75-cm$^2$ tissue culture flasks were grown to confluence in Ham's F-12 medium containing 20% FBS. The original culture medium was then replaced with Ham's F-12 for 24 hours and was subsequently changed to F-12 containing either of the following: 1) 10% human serum containing immunoglobulin (IgE) E at greater than 1000 IU/ml obtained from allergic patients with moderate to severe asthma (as above); 2) 10% human serum obtained from non-atopic non-asthmatic (control) individuals (Hakonarson et al., 1996, J. Clin. Invest. 97:2593–2600); 3) IgE immune complexes (15:5 µg/ml), or; 4) F-12 alone, for the various time points.

Pharmacodynamic Studies

Following incubation of the tissue preparations obtained as described herein, each rabbit airway segment was suspended longitudinally between stainless steel triangular supports in siliconized Harvard 20 ml organ baths. The lower support was secured to the base of the organ bath, and the upper support was attached via a gold chain to a Grass FT.03C force transducer from which isometric tension was continuously displayed on a multichannel recorder. Care was taken to place the membranous portion of the trachea between the supports in order to maximize the recorded tension generated by the contracting trachealis muscle. The tissues were bathed in modified Krebs-Ringer solution containing 125 mM NaCl, 14 mM NaHCO$_3$, 4 mM KCl, 2.25 mM CaCl$_2$.H$_2$O, 1.46 MgSO$_4$.H$_2$O, 1.2 mM NaH$_2$PO$_4$.H$_2$O and 11 mM glucose. The baths were aerated with 5% CO$_2$ in oxygen, a pH of 7.35–7.40 was maintained, and the organ bath temperature was held at 37° C. Passive resting tension of each TSM segment was set at 2.0 g after each tissue had been passively stretched to a tension of 8 g in order to optimize the resting length of each segment as described (Tanaka et al., 1990, J. Clin. Invest. 85:345–350). The tissues were allowed to equilibrate in the organ baths for 45 minutes, at which time each tissue was primed with a 1 minute exposure to $10_{-4}$ M acetylcholine (ACh). Cholinergic contractility was subsequently assessed in the TSM segments by cumulative administration of ACh in final bath concentrations ranging from $10^{-10}$–$10^{-3}$ M. Thereafter, in separate studies, relaxation dose-response curves to isoproterenol ($10^{-10}$–$10^{-4}$ M) were conducted in tissues half-maximally contracted with ACh. The relaxant responses to isoproterenol were analyzed in terms of % maximal relaxation (Rmax) from the active cholinergic contraction, and sensitivity to the relaxing agent was determined as the negative logarithm of the dose of the relaxing agent producing 50% of Rmax (pD$_{50}$) (i.e., geometric mean ED$_{50}$ value).

Characterization of Fc Receptor mRNA by Reverse Transcriptase Polymerase Chain Reaction (RT-PCR)

Total RNA was isolated from sensitized and control ASM cells and tissue using the modified acid guanidinium thiocyanate phenol-chloroform extraction method (Chomczynski et al., 1987, Anal. Biochem. 162:156–159) which includes proteinase K (in 0.5% SDS) digestion of protein in the initial RNA pellet. The concentration of each RNA sample was then determined spectrophotometrically. This procedure consistently yielded 20–25 µg of intact RNA per each T-75 flask of ASM cells.

To analyze mRNA expression specific for the FcγRIa, R-IIa, -IIc, -IIb, -RIII, and FcεRII receptor subtypes, an RT-PCR protocol and human-specific primers for these Fc receptor subtypes was used. cDNA was synthesized using 2.5 µg of total RNA isolated from the cell and tissue samples following 0, 6 and 24 hours of treatment with either 10% control or 10% atopic asthmatic human serum in the presence or absence of an anti-CD23 blocking antibody, and using RNA from cells treated with IgE immune complexes or F-12 serum-free medium alone. cDNA generated using RNA obtained from immortalized U937 cells and the B cell line 8.1.6, were used as positive controls for FcγRIII and FcεRII mRNA expression, respectively. The cDNA was primed with oligo (dT) 12–18 and with random hexamer nucleotides (N6) in the absence of signal using the former method. Two µl of cDNA was used in each PCR reaction. The Fc receptor primers used in the PCR assays were based on the published sequences of the human Fcγ-RI, -RII, -RIII and FcεRII genes (Capel et al., 1994, Immunometh. 4:25–34; Kikutani et al., 1986, Cell 47:657–665) and included the following primer sets:

FcγRI: 5' Primer:
5'-ATGTGGTTCTTGACAACTCTGCTC 3'
(SEQ ID NO:1)
3' Primer: 5'-ATGTCTGTCTTCTTGAAGGCTGGA-3'
(SEQ ID NO:2)
(the amplification product is 1,038 bp)

FcγRIIa,c: 5' Primer: 5'-GACTCCATTCAGTGGTTCCA-3' (SEQ ID NO:3)

3' Primer: 5'-GTCAGCTGTTTCATAGTCATTG-3' (SEQ ID NO:4)

(the amplification product is 644 bp)

FcγRIIb: 5' Primer: 5'-GACTCCATTCAGTGGTTCCA-3 (SEQ ID NO:5)

3' Primer: 5'-CCCAACTTTGTCAGCCTCATC-3' (SEQ ID NO:6)

(the amplification product is 618 bp)

FcγRIII: 5' Primer: 5'-AAGATCTCCCAAAGGCTGTG-3' (SEQ ID NO:7)

3' Primer: 5'-ATGGACTTCTAGCTGCACCG-3' (SEQ ID NO:8)

(the amplification product is 254 bp)

FcεRII: 5' Primer: 5'-CGTCTCTCAAGTTTCCAAG-3' (SEQ ID NO:9)

3' Primer: 5'-GCACTTCCGTTGGGAATTTG-3' (SEQ ID NO:10)

(the amplification product is 333 bp)

Rabbit specific a-actin primers, 5'-CGACATCAAGGAGAAGCTG-3' (SEQ ID NO:11) and 5'-CTAGAAGCATTTGCGGTGC-3' (SEQ ID NO:12) (19 mers), and human specific ribosomal protein L7 (RPL7) primers 5'-AAGAGGCTCTCATTTTCCTGGCTG-3' (SEQ ID NO:13) (24 mer) and 5'-TCCGTTCCTCCCCATAATGTTCC-3' (SEQ ID NO: 14) (23 mer), based on the published sequence of the rabbit α-actin (Putney et al., 1983, Nature 302:718–721) and human RPL7 genes (Seshadri et al., 1993, J. Biol. Chem. 268:18474–18480), respectively, were used to assess general transcription levels in each sample. The cycling profile used was as follows: Denaturation: 95° C. for 1 minute; annealing: 54° C. for 1 minute; and extension: 72° C. for 1–2 minutes using 40 cycles for the FcγRI, RII, RIII and FcεRII genes; and using 22 cycles for the α-actin and RPL7 genes, respectively. The number of cycles was determined to be in the linear range of production of the PCR product. The PCR reactions using the human Fcγ, Fcε, RPL7, and rabbit α-actin primers were performed using equivalent amounts of cDNA prepared from 2.5 μg of total RNA. Equal aliquots of each PCR reaction were then run on a 1.2% agarose gel and were subsequently transferred to a Zeta-probe membrane overnight in 0.4 N NaOH. Following capillary transfer, the DNA was immobilized by UV-crosslinking using a Stratalinker UV Crosslinker 2400 at 120,000 microjoules/cm$^2$ (Stratagene, La Jolla, Calif.).

Prehybridization in a Techne hybridization oven was conducted for 2–3 hours at 42° C. in 50% formaldehyde, 7% (w/v) SDS, 0.25 M NaCl, 0.12 M Na$_2$HPO$_4$ (pH 7.2), and 1 mM EDTA. Hybridization was for 20 hours at 42° C. in the same solution. The FcγRI, RII, RIII; FcεRII; RPL7 and α-actin DNA levels were assayed by Southern blot analysis using $^{32}$P-labeled probes. The FcγRIII, α-actin and RPL7 probes were prepared by pooling several RT-PCR reactions which used the FcγRIII, α-actin and RPL7 PCR fragments and purifying them from a 1.2% agarose gel using Qiaex II agarose gel extraction kit. The FcγRIII, α-actin and RPL7 cDNA fragments were subsequently sequenced for product confirmation. The other individual human Fcγ and Fcε probes were obtained from the cloned cDNA sequences of these genes. In addition, the 333 bp rabbit ASM CD23 RT-PCR products were also sequenced for product confirmation, and exhibited approximately 90% homology with the human CD23 B-lymphocyte receptor gene. Washes were as follows: 1×15 minutes in 2×SSC, 0.1% SDS; 1×15 minutes in 0.1×SSC, 0.1% SDS both at room temperature, and 2×15 minutes at 50° C. in 0.1×SSC, 0.1% SDS. Southern blots were quantitated by direct measurements of radioactivity in each band using a PhosphoImager (Molecular Dynamics, Sunnyvale, Calif.).

Determination of Fc Receptor Expression in ASM Cells and Tissue

Fc receptor cell surface expression was examined in cultured rabbit ASM cells using a Coulter EPICS Elite flow cytometer (Coulter EPICS Division, Hialeah, Fla.) equipped with a 5 watt argon laser operated at 488 nM and 300 mwatt output. Fluorescence signals were accumulated as two parameter fluorescence histograms wherein both % positive cells and mean channel fluorescence were recorded. Cells which were treated for 24 hours with either 10% atopic asthmatic or 10% control human serum were resuspended in buffer, dispersed by passage through a 23 g needle, and then stained with the individual antibodies. Based on the results of the Fc receptor mRNA expression studies, the targeted monoclonal antibodies used included the 3G8-FITC anti-FcγRIII (Medarex, Inc., Annandale, N.J.) and the FITC mouse monoclonal antibody to human CD23 (Calteg, San Francisco, Calif.). The immortalized B-cell line 8.1.6, was used as the positive control for the CD23 receptor expression assay. The cells were also stained with FITC- and PE-conjugated mouse antibodies having the identical isotypes as the Fc receptor monoclonals to measure background fluorescence (i.e., IgG$_3$-FITC as control for anti-CD23; and IgG$_2$a-PE as control for FcγRIII, respectively). The antibody-stained cells were then evaluated by flow cytometry and were analyzed using the Elite Immuno 4 statistical software (Coulter EPICS Division, Hialeah, Fla.). Fluorescence intensities were expressed as % positive cells, including mean channel fluorescence.

An immunofluorescence detection assay was also used to examine for FcεRII surface receptor expression in rabbit ASM cells and tissue following 24 hours of treatment with human control vs. atopic asthmatic serum, as described above. The ASM cells were fixed in acetone alone, whereas the tissues were embedded in OCT compound (Miles Laboratories) and frozen in acetone/dry.ice. Serial 3–5 μm TSM sections were prepared and mounted on poly-L-lysine coated slides. The specimens were incubated with PBS buffer containing 10% rabbit serum to suppress non-specific staining and were subsequently labeled overnight at 4° C. with primary mouse anti-human CD23 (FcεRII) antibody at a 1:250–500 dilution. In control sections, the primary antibody was replaced by immunoglobulins of the same isotype following the manufacture's protocol (mouse IgGl negative control). Parallel cell and tissue slides were also stained with an α-actin antibody. After subsequent repeat washing, FITC-labeled F(ab')$_2$ goat anti-mouse IgE (Fcε) fragments was added as the secondary antibody. The mixtures were incubated for 1 hour in 1:500–1000 dilutions in PBS containing 0.5% BSA. After serial washing, the slides were examined using a fluorescent microscope, and quantitative analysis of the protein localization in the cell and tissue sections under the above experimental conditions was performed using the Metamorph Imaging System interfaced with a Nikon Diaphot 300 Image Analyzer that utilizes a Hamamatsu CCD camera.

Statistical Analysis

Unless otherwise indicated, results are expressed as mean±SE. Statistical analysis was performed by means of two-tailed paired Student's t-test. P-values<0.05 were considered significant.

Reagents

The Fcγ-RI, -RII, -RIII, FcεRII, RPL7 and rabbit α-actin primers were obtained from Integrated DNA Technologies Inc., Coralville, Iowa. ACh and isoproterenol hydrochloride were obtained from Sigma Chemical Co. (St. Louis, Mo.). The human IgG, goat-antihuman IgG, human myeloma IgE, and the goat-antihuman IgE antibodies were purchased from Biodesign Int. (Kennebunk, Me.). The 3G8-FITC anti-FcγRIII and FITC-mouse monoclonal antibody to the human CD23 receptors used in flow cytometric studies were purchased from Medarex, Inc. (Annandale, N.J.), and Calteg (San Francisco, Calif.), respectively. The anti-CD23 monoclonal blocking antibody (mAb135) is described in Mossalayi et al. (1992, EMBO J. 11:4323–4328). The FcεRII (CD23) antibody and F(ab')$_2$-FITC fragments used in the immunofluorescence studies were purchased from Serotec Ltd. (Oxford, UK). The immortalized B-cell line 8.1.6, is described in Weenink et al. (1977, International Immunol. 9(6):889–896). The Fcγ-RI, -RII -RIII and FcεRII cDNA probes are described in McKenzie (1994, Current Opinion in Hematol. 1:45–52). All drug concentrations are expressed as final bath concentrations. Isoproterenol and ACh were made fresh for each experiment, dissolved in normal saline to prepare $10^{-4}$ M and $10^{-3}$ M solutions, respectively. The human tissue was provided by the Cooperative Human Tissue Network which is funded by the National Cancer Institute.

The Results of the experiments presented in this Example are now described.

Figure 1A:
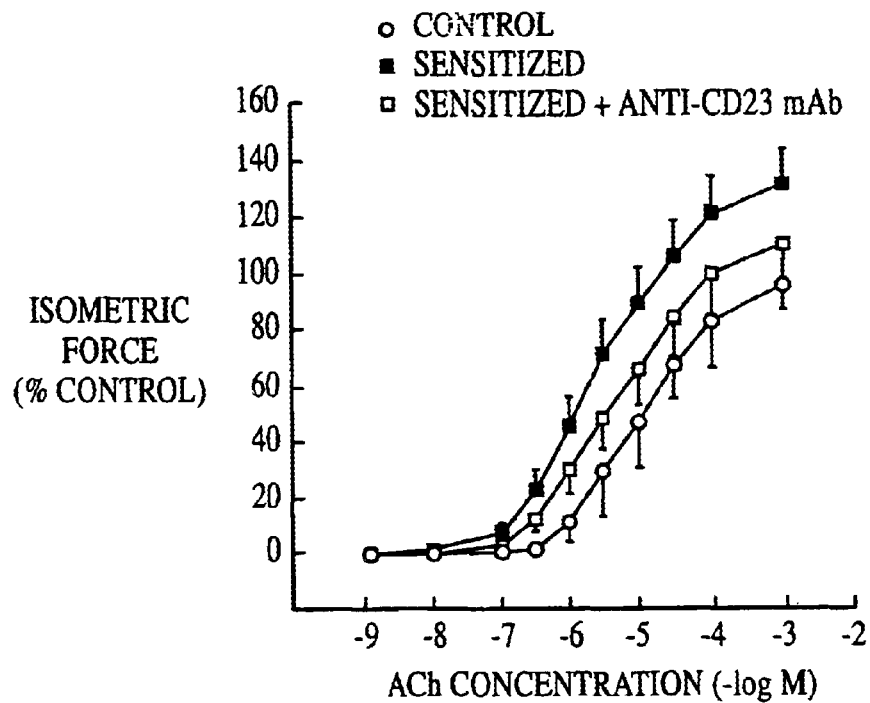
FIG. 1A is a graph depicting a comparison of contractile dose-response relationships to acetylcholine (ACh) in paired control serum-treated (open circles) and atopic asthmatic serum-treated tracheal smooth muscle (TSM) segments in the absence (closed circles) and presence (open squares) of anti-CD23 monoclonal antibody (MAb).
Figure 1B:
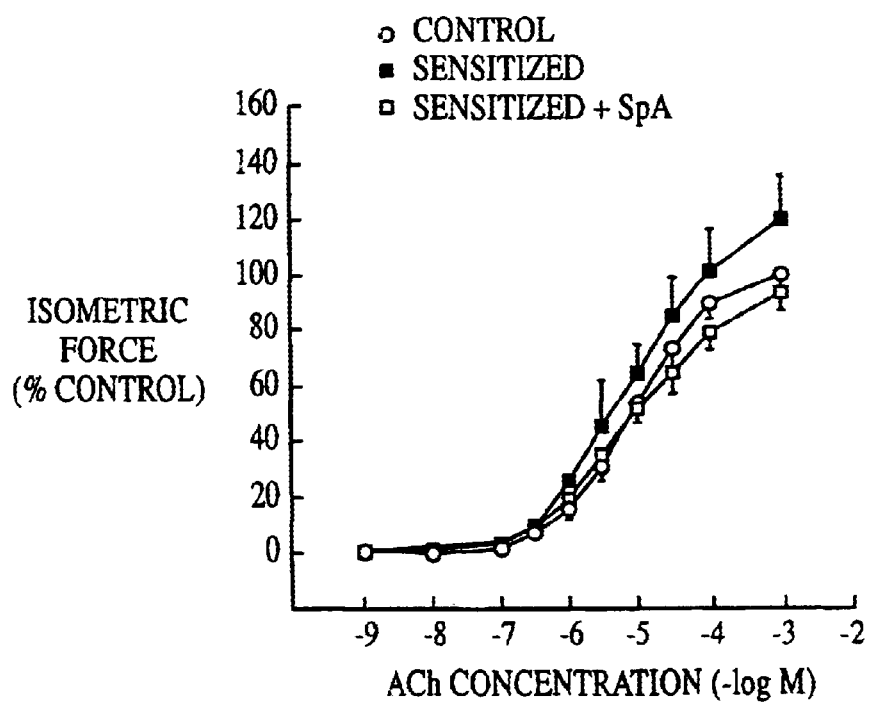
FIG. 1B is a graph depicting a comparison of contractile dose-response relationships to augmented constrictor responses (ACR) in control serum-treated (open circles) and atopic asthmatic serum-treated TSM in the absence (closed circles) and presence (open squares) of Staphylococcus protein A (SpA). Data represent mean±SE values from 6 paired tissue samples.

Role of Fc Receptors in Altered Responsiveness of Atopic Asthmatic Sensitized Airway Smooth Muscle Passive sensitization of isolated naive airway smooth muscle (ASM) tissue with human atopic asthmatic serum induces changes in the tissue's agonist-mediated constrictor and relaxant responsiveness that phenotypically resemble the pro-asthmatic state (Hakonarson et al., 1995, Am. J. Physiol. (Lung Cell Mol. Physiol.) 269: L645–L652). To examine whether these effects of atopic asthmatic serum are mediated, at least in part, by the presence of elevated levels of IgE in the sensitizing serum, constrictor and relaxation responses were separately examined in TSM segments that were treated with human control or atopic asthmatic serum in the absence and presence of a blockade of specific Fc receptors, or following depletion of immune complexes in the sensitizing serum by treatment with Sepharose Staphylococcus protein A (SpA) (Kessler, 1975, J. Immunol. 115:1617–1624). As shown in FIG. 1, relative to tissues incubated with control serum (open circles), the maximal constrictor (Tmax) responses to ACh were significantly enhanced in TSM passively sensitized with atopic asthmatic serum (filled circles). Accordingly, the mean±SE Tmax values amounted to 121.7±5.3 and 146.0±15.5 g/g TSM weight in the control and sensitized tissues, respectively (p<0.01). The induced augmented constrictor responses to ACh, however, were largely prevented in atopic serum-sensitized tissues that were pre-treated with an anti-CD23 monoclonal blocking antibody (anti-CD23 MAb) (FIG. 1A; open squares) or when the sensitizing serum was depleted of its immune complexes by pre-treatment with SpA (FIG. 1B; open squares).

Figure 2A:
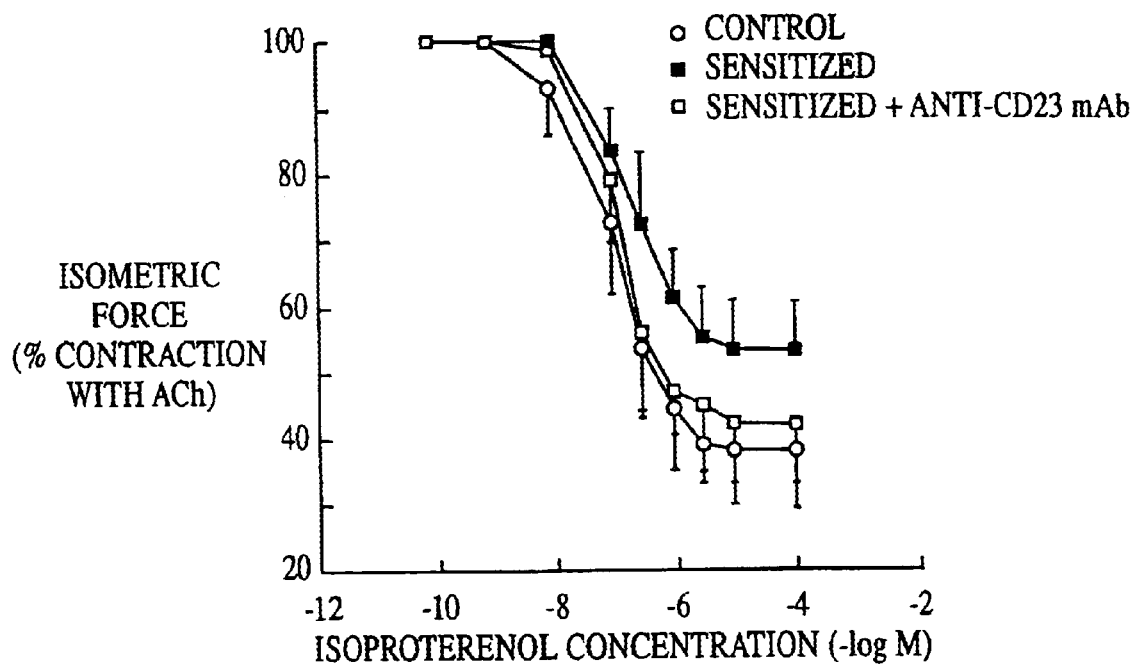
FIG. 2A is a graph depicting a comparison of relaxation dose-relationships to isoproterenol in paired control serum-treated (open circles) and atopic asthmatic serum-treated TSM segments half-maximally contracted with their respective $ED_{50}$ doses of ACh in the absence (filled circles) and presence (open squares) of anti-CD23 MAb.
Figure 2B:
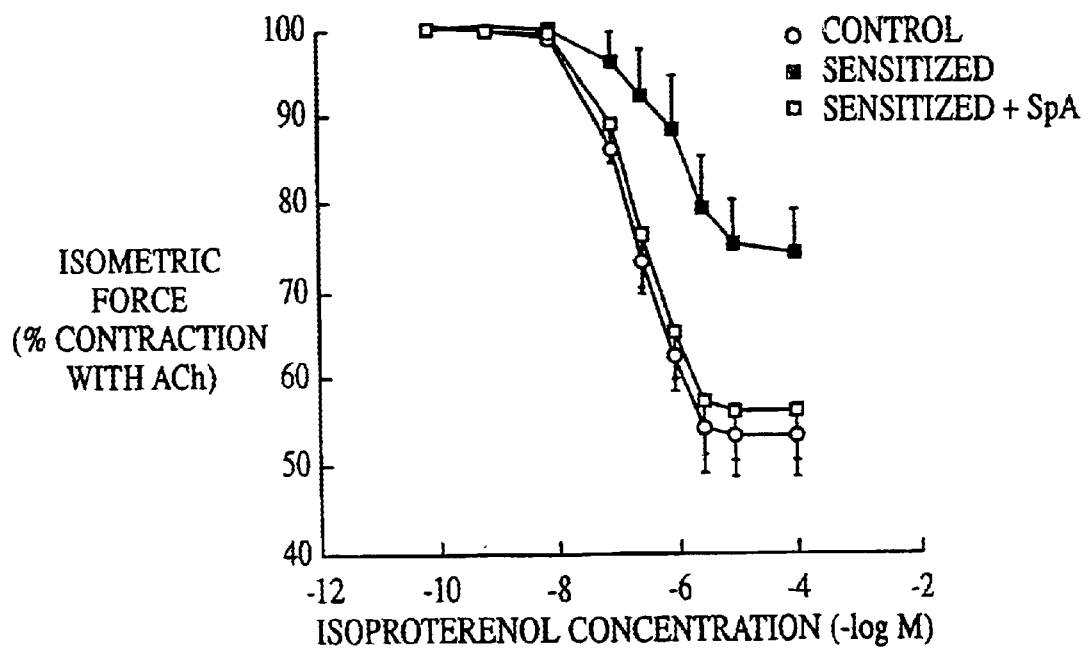
FIG. 2B is a graph depicting a comparison of relaxation responses to isoproterenol in control (open circles) and atopic asthmatic serum-treated TSM in the absence (filled circles) and presence (open squares) of SpA. Data are mean±SE values from 8 paired tissue samples.

In separate studies, during comparable levels of initial sustained ACh-induced contractions in atopic asthmatic sensitized and control serum-treated airway segments, averaging 38 and 43% of Tmax, respectively, administration of the beta-adrenergic receptor agonist, isoproterenol, elicited cumulative dose-dependent relaxation of the pre-contracted TSM segments (FIG. 2). Relative to control TSM, the maximal relaxation responses (Rmax) and sensitivities (pD$_{50}$, i.e., $-\log$ ED$_{50}$) to isoproterenol were significantly attenuated in the atopic asthmatic serum-sensitized TSM. Accordingly, the mean Rmax values for isoproterenol amounted to 26.0±5.1% in the atopic sensitized TSM, compared to 47.0±4.7% in the control serum-treated TSM (p<0.005), with corresponding pD$_{50}$ values averaging 5.82±0.16 and 6.59±0.11 $-\log$ M, respectively (p<0.005). However, the attenuated isoproterenol-induced relaxation responses were ablated in atopic serum-sensitized TSM that were pretreated with anti-CD23 MAb (FIG. 2A), or when the sensitizing serum was initially depleted of its immune complexes with SpA (FIG. 2B).

In contrast to the above observations obtained in atopic asthmatic serum-sensitized TSM, in tissues incubated with control serum, neither anti-CD23 MAb nor pretreatment of the control serum with SpA affected the subsequent contractility of the tissue to ACh or relaxation responsiveness to isoproterenol. Moreover, contrasting the above inhibitory effects of anti-CD23 MAb in atopic sensitized TSM, exposure of the sensitized tissues to a monoclonal blocking antibody, to the FcγRIII receptor, which is also expressed in ASM (see below), had no appreciable effect on the heightened constrictor responsiveness of the tissue to ACh or attenuated relaxation to isoproterenol.

Effects of IgE and IgE Immune Complexes on ASM Responsiveness.

Figure 3:
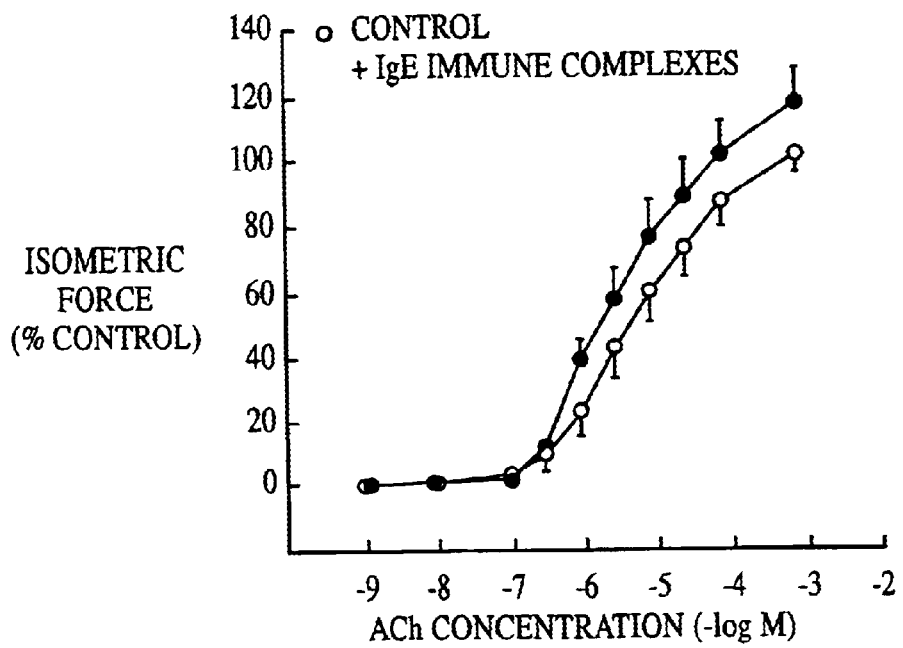
FIG. 3 is a graph depicting a comparison of airway constrictor responses to ACh in isolated paired TSM segments in the absence (open circles) and presence (filled circles) of IgE immune complexes. Data represent mean±SE values from 6 paired tissue samples.

In light of the above observations suggesting a role for an IgE immune complex/FcεRII receptor interaction in mediating altered ASM responsiveness in the atopic asthmatic sensitized state, the issue of whether the sensitizing effects of the atopic asthmatic serum could be simulated by treatment of naive TSM with either exogenous IgE or IgE immune complexes was examined. Constrictor and relaxant dose-response relationships to ACh and isoproterenol, respectively, were separately compared in TSM exposed for 24 hours to vehicle alone (control) or varying concentrations of IgE or IgE immune complexes. Relative to their respective controls, the maximal constrictor responses to ACh were significantly (p<0.05) enhanced in tissues treated for 24 hours with an optimal concentration of IgE immune complexes (i.e., 15:5 μg/ml of IgE/anti-IgE), wherein the mean±Tmax responses-amounted to 108.8±10.2 versus 94.2±5.1 g/g TSM weight obtained in the control tissues (FIG. 3). Comparably, during similar initial sustained levels of ACh-induced contractions (i.e., approximately 45% Tmax), the subsequent relaxation responses to cumulative administration of isoproterenol were markedly reduced in the IgE immune complex-treated vs. control tissues (FIG. 4), wherein the Rmax responses amounted to 36.8±10.4 vs. 67.8±6.0%, respectively (p<0.05), and the corresponding pD$_{50}$ values averaged 6.70±0.08 and 6.84±0.11 $-\log$ M, respectively (p<0.05). Qualitatively, similar results were obtained in tissues treated with IgE alone, although the changes in ACh-induced contraction and attenuation of isoproterenol-induced relaxation in these tissues were quantitatively less pronounced than those obtained in IgE immune complex-treated TSM.

Fc Receptor Expression in Atopic Asthmatic Sensitized Airway Smooth Muscle

In extending the above pharmacodynamic studies, in separate experiments, the issues of whether cultured ASM cells and isolated ASM tissue express Fc receptors and whether the expression of these receptors is modulated in the atopic asthmatic sensitized state was examined. Using RT-PCR and Fc receptor specific primers for the different Fcγ and Fcε receptor subtypes, cDNA was reverse transcribed from total isolated RNA primed with random hexamer primers, and Southern blots were probed with human cDNA probes specific for individual Fcγ and Fcε receptor genes as described in the Methods section. A 415-bp α-actin probe was also used to control for gel loading, and the signals for the Fcγ, Fcε and α-actin PCR products were quantitated on a Phosphorimager.

In contrast to the lack of detectable expression of FcγRI and FcγRII specific mRNA, ASM cells expressed mRNA specific for the FcγRIII receptor (FIG. 5A). In parallel with the unaltered constitutive expression of α-actin mRNA, the FcγRIII signal did not temporally vary in cells treated for up to 24 hours with either control or atopic sensitized serum, and there were no significant differences in FcγRIII mRNA expression between control and sensitized cells. Expression of the high affinity IgE receptor, FcεRI, was also undetectable in the ASM cells. On the other hand, as shown in FIG. 5B, expression of mRNA specific for the low affinity IgE receptor, FcεRII (i.e., CD23), was detected in both the control and atopic asthmatic sensitized cells. Moreover, in contrast to control serum-treated ASM cells wherein the mRNA signal did not systematically vary with time, the intensity of the FcεRII mRNA signal progressively increased at 6 and 24 hours in the atopic asthmatic serum-sensitized cells. Thus, rabbit ASM cells expressed mRNA specific for both the low-affinity FcγRIII and FcεRII receptors as verified by the presence of 254 bp (FcγRIII) and 333 bp (FcεRII) cDNA fragments. In contrast to FcγRIII, expression of FcεRII was significantly upregulated at 24 hr (i.e., >2 fold) following treatment with atopic asthmatic serum.

Similar results were obtained in comparable experiments conducted on isolated human tracheal smooth muscle tissue wherein adjacent alternating sections were exposed for 24 hours to either control or atopic asthmatic serum. Following RNA extraction, PCR products generated using oligo (dT)-primed human cDNA and the above human-specific FcγRIII and FcεRII primers, as well as a primer for the constitutively expressed ribosomal protein, RPL7, were loaded in separate lanes on a 1.2% agarose gel. The Southern blots were then analyzed using $^{32}$P-labeled human-specific FcγRIII, FcεRII, and RPL7 (157-bp) probes. As depicted in FIG. 6, following 24 hours of incubation with serum, the signals for expression of FcγRIII and RPL7 mRNA were similar in the control (CO) and atopic asthmatic-sensitized (SE) tissue samples (FIG. 6A). In contrast, the signal for FcεRII mRNA expression, although detectable in the control samples, was markedly induced in the atopic asthmatic serum-treated tissues (FIG. 6B), whereas that of RPL7 was unaffected in these cells. Thus, a marked induction of FcεRII expression was observed in the atopic asthmatic serum-sensitized sample (i.e., >7.5 fold), whereas expression of FcγRIII or RPL7 was similar in both samples.

In light of the above observations, together with the preceding pharmacodynamic findings implicating a role for IgE immune complex/CD23 interaction in mediating the changes in agonist responsiveness in the atopic asthmatic sensitized tissues (FIGS. 1 and 2), the issue of whether the observed upregulation of FcεRII expression in the atopic asthmatic sensitized state was attributable to activation of the FcεRII receptor was examined. As shown in FIG. 7, using ASM tissue sections isolated from the same human lung specimen it was discovered that, whereas the tissue samples exposed to atopic asthmatic serum (SE) displayed markedly induced FcεRII expression relative to control (CO) serum-treated samples, the upregulation of FcεRII expression was largely inhibited by pretreatment of the atopic serum-sensitized tissues with anti-CD23 monoclonal antibody (SE$^+$). Thus, anti-CD23 MAb significantly attenuated the induction of FcεRII mRNA expression at 24 hours in atopic asthmatic-serum sensitized airway smooth muscle. Moreover, in separate complimentary experiments examining the effects of exogenous administration of IgE immune complexes on FcεRII expression in cultured ASM cells, the data disclosed demonstrate that treatment of the cells with IgE immune complexes induced progressive enhancement of FcεRII mRNA expression (FIG. 8A), resulting in a near 5-fold increase in FcεRII expression at 24 hours (FIG. 8B). Additionally, in concert with the above ASM tissue studies, pretreatment of cells with anti-CD23 monoclonal antibody significantly inhibited (i.e., by approximately 40%) the magnitude of the IgE immune complex-induced FcεRII expression at 24 hours (FIG. 8B). Thus, a progressive induction of FcεRII mRNA expression up to 24 hours was observed following treatment with IgE immune complexes, and inhibition of FcεRII expression at 24 hr in the presence of anti-CD23 MAb (hatched bar) was observed.

Taken together, the above observations demonstrate that rabbit and human ASM express mRNA specific for the low-affinity FcγRIII and FcεRII receptors for IgG and IgE, respectively, and that the expression of the FcεRII receptor mRNA, as examined using RT-PCR, is upregulated by treatment with either human atopic asthmatic serum or exogenously administered IgE immune complexes, secondary to activation of the endogenously expressed FcεRII receptor.

Expression of FcγRIII and FcεRII Cell Surface Proteins in Sensitized Airway Smooth Muscle Given the above findings, the issue of whether ASM cells express FcγRIII and FcεRII receptor proteins on the cell surface was examined by flow cytometry. As shown in FIG. 9, ASM cells expressed both the low-affinity FcγRIII (FIG. 9A) and FcεRII (FIG. 9B) receptors as surface protein. In contrast to unaltered FcγRIII receptor expression after exposure of the cells for 24 hours to control or atopic asthmatic serum (FIG. 9A), cell surface expression of the FcεRII receptor was increased by >2-fold in the atopic asthmatic serum-treated vs. control serum-treated cells (FIG. 9B). Thus, rabbit ASM cells expressed surface protein specific for both FcγRIII and FcεRII receptors. In contrast to FcγRIII receptor expression which was unaltered in the presence of atopic asthmatic serum, expression of the FcεRII receptor was increased by >two-fold (i.e., from 17 to 36%) in the presence of atopic asthmatic serum.

To further substantiate the above observations, sensitized ASM cells and tissue were subsequently examined for evidence of altered FcεRII receptor expression by immunofluorescence staining. As shown in FIG. 10, relative to an isotype negative control antibody (upper panels: A and B), FcεRII staining with an anti-CD23 antibody was weakly positive both in control (CO) serum-treated cells and tissue (lower left panels: A and B). Moreover, in parallel with the above results based on flow cytometric analysis, surface staining for the CD23 receptor protein was notably enhanced in the atopic asthmatic serum-treated cells and tissue (FIG. 10; lower right panels: A and B). Thus, significantly enhanced FcεRII (CD23) receptor staining in ASM cells and tissue treated with atopic asthmatic serum (i.e., lower SE panels in Panel A and Panel B) was observed.

Previous studies have implicated both mast cells and other pro-inflammatory cells in the pathogenesis of asthma. However, the present study addresses the novel hypothesis that the resident airway smooth muscle itself also plays an etiologic role in the pathobiology of the disease. The data disclosed herein provide compelling new evidence demonstrating that: 1) ASM cells express mRNA and surface protein for the low-affinity FcγRIII (CD16) and FcεRII (CD23) receptors for IgG and IgE, respectively; 2) in contrast to the FcγRIII receptor, expression of the FcεRII receptor is significantly upregulated following treatment with either atopic asthmatic serum or IgE immune complexes, a finding similar to that obtained in a passively sensitized human ASM; 3) the induced changes in FcεRII receptor expression are associated with altered ASM responsiveness to muscarinic/cholinergic and β-adrenoceptor activation in the atopic asthmatic sensitized state; and 4) the latter changes in FcεRII receptor expression and responsiveness in atopic asthmatic sensitized ASM can be attributed to activation of intrinsically expressed FcεRII receptors by immune complexed IgE.

The use of passive sensitization of rabbit and human isolated airways with human atopic asthmatic serum provides a practical in vitro experimental approach to examine the regulation of airway responsiveness in the atopic asthmatic state (Hakonarson et al., 1997, J. Clin. Invest. 99:117–124; Hakonarson et al., 1995, Am. J. Physiol. (Lung Cell Mol. Physiol.) 269:L645–L652). In this regard, the observed changes in responsiveness in the atopic sensitized tissues closely mimicked the perturbations in airway function that characterize the in vivo asthmatic condition, including exaggerated bronchoconstrictor responsiveness to contractile agonists and impaired airway relaxation to β-adrenoceptor stimulation (Hakonarson et al., 1997, J. Clin. Invest. 99:117–124; Hakonarson et al., 1995, Am. J. Physiol. (Lung Cell Mol. Physiol.) 269:L645–L652). When the mechanistic link between exposure of naive airway tissue to atopic asthmatic serum and its resultant altered responsiveness was examined using the same experimental model described herein, it was observed that the latter effect was largely mediated by the induced autologous expression and autocrine action of the cytokine, IL-1β, in atopic sensitized ASM (Hakonarson et al., 1997, J. Clin. Invest. 99:117–124). Moreover, the mechanism of action of IL-1β in eliciting the altered responsiveness in sensitized tissues was attributed to its induced upregulated expression of $G_i$ protein, specifically $Giα_2$ and $Giα_3$ which inhibit intracellular cAMP accumulation (Hakonarson et al., 1996, J. Clin. Invest. 97:2593–2600).

The data presented herein establish that the sequence of events leading to cytokine-induced changes in ASM responsiveness in the sensitized state is initiated by IgE-coupled FcεRII receptor activation involving the ASM itself. The present observations demonstrate that either depletion of serum immune complexes or pretreatment with a specific anti-CD23 monoclonal blocking antibody largely prevented the changes in ASM responsiveness induced by exposure of the tissues to atopic asthmatic serum (FIGS. 1 and 2). Furthermore, in complimentary studies, exposure of naive ASM tissue to IgE immune complexes produced changes in ASM responsiveness (FIGS. 3 and 4) which closely resembled those observed in the atopic sensitized state. Thus, IgE-coupled Fc receptor activation principally involving the FcεRII receptor in ASM itself appears to be fundamentally responsible for producing the perturbations in airway responsiveness that characterize the pro-asthmatic state.

In concert with the above pharmacodynamic results, additional experiments demonstrated the presence of constitutive FcεRII and FcγRIII receptor mRNA and cell surface expression, both in cultured ASM cells and human ASM tissue (FIGS. 5 and 6). Furthermore, in contrast to FcγRIII expression, which was unaltered in the presence of atopic asthmatic serum, expression of FcεRII was markedly enhanced in ASM exposed to the sensitizing atopic serum (FIGS. 5 and 6). In considering these results, it is relevant to note that a number of studies have reported a direct correlation between serum IgE levels and FcεRII and -RI expression (Spiegelberg et al., 1981, J. Clin. Invest. 68:845–852; Conroy et al., 1977, J. Immunol. 118:1317–1321; Malveaux et al., 1978, J. Clin. Invest. 62:176–181). While these reports raised the notion of a possible common mechanism regulating the production of both IgE and its receptors, more recent evidence based on studies using different cell lines suggests that IgE itself may enhance FcεRI (Lantz et al, 1997, J. Immunol. 158:2517–2521; Yamaguchi et al., 1997, J. Exp. Med. 185:663–672) or FcεRII expression (Lee et al., 1987, J. Immunol. 139:1191–1198; Daeron et al., 1986, J. Immunol. 136:1612–1619; Lee et al., 1986, J. Immunol. 136:4573–4580). The latter concept is supported by the present experiments, wherein it was observed that the induced expression of FcεRII in ASM treated with atopic asthmatic serum was largely inhibited in the presence of an anti-CD23 blocking antibody (FIG. 7). Moreover, as further support for the concept of IgE-dependent modulation of FcεRII expression, it was also observed that exogenously administered IgE immune complexes elicited an increase in FcεRII expression (FIG. 8A) and, further, that this effect was significantly inhibited by pretreatment with anti-CD23 MAb (FIG. 8B). Thus, the data presented herein are consistent with the presence of a positive feedback system in ASM wherein IgE upregulates the expression of its own low affinity receptor. This notion is in general agreement with previous studies which reported the presence of IgE-dependent Fcε receptor induction in other cell types (Lantz et al., 1997, J. Immunol. 158:2517–2521; Yamaguchi et al., 1997, J. Exp. Med. 185:663–672; Lee et al., 1987, J. Immunol. 139:1191–1198; Daeron et al., 1986, J. Immunol. 136:1612–1619; Lee et al., 1986, J. Immunol. 136:45734580). However, in these earlier studies mRNA levels for Fcε receptor expression were not examined, and the increased cell surface expression of the receptor was attributed to IgE-mediated inhibition of proteolytic cleavage of the receptor from its membrane binding site (Lee et al., 1987, J. Immunol. 139:1191–1198). Recognizing the limitations in quantitative analysis using RT-PCR, the present observations demonstrating the presence of IgE-dependent enhanced expression of FcεRII mRNA suggest that IgE exerts its upregulatory action on FcεRII expression, at least in part, via a pre-translational effect.

In recent years, the complexity of transmembrane signaling via the FcεRII receptor has been partially unraveled. In this regard, together with IgE binding, signaling via the FcεRII receptor is known to include coupling of the receptor to complement receptor 2 (CR2), also referred to as CD21, which is a receptor for fragments of the complement component, C3 (Aubry et al., 1992, Nature 358:505–507). Further, as demonstrated in B-lymphocytes, CR2 co-ligates with the membrane protein, CD19 and, in the presence of C3 fragments bound to antigen/immune complexes (e.g., IgE/ IgG and/or IgM), this membrane-linked network of molecules acts synergistically to mediate the cytokine activities of FcεRII (Sutton et al., 1993, Nature 366:421–428; Delespesse et al., 1992, Immunol. Rev. 125:77–97; Matsumoto et al., 1991, J. Exp. Med. 173:55–64). Accordingly, in B-lymphocytes, this antigen/IgE immune complex network coupled to the FcεRII receptor apparently serves to facilitate antigen presentation to antigen-specific CD4+(helper)

T-lymphocytes, a process resulting in the expression of the CD4+/Th2 phenotype. The latter phenomenon is associated with the release of such Th2-derived cytokines as IL-4 and IL-5 which are involved in B-lymphocyte switching to IgE production and eosinophil accumulation, respectively (Delespesse et al., .1992, Immunol. Rev. 125:77–97). With potential implications related to asthma, recent evidence based on studies conducted in house dust mite-immunized mice suggests that the above mechanism of IgE/FcεRII-coupled facilitation of antigen presentation to T-lymphocytes is important for both the induction of the Th2-type immune response in the lungs and the subsequent infiltration of eosinophils into the airways following inhaled antigen challenge (Coyle et al., 1996, J. Exp. Med. 183:1303–1310).

In light of the above evidence regarding the role of CD23 receptor activation in eliciting Th-2 cytokine production and pulmonary eosinophilic infiltration in the antigen-sensitized state, the results of the present study raise the consideration that, apart from inducing changes in airway responsiveness, upregulated FcεRII expression and activation in airway smooth muscle cells may also play a role in modulating local airway immune responses. Indeed, this compelling concept is in part supported by the recent observation that airway smooth muscle cells are autologously induced to release IL-1β in the atopic asthmatic sensitized state (Hakonarson et al., 1997, J. Clin. Invest. 99:117–124), a finding which, together with the present observations, suggests the presence of FcεRII-coupled local stimulation of cytokine release and signaling. In this context, it is important to note that we have discovered that IgE-coupled activation of FcεRII receptors in airway smooth muscle can also induce the release of Th-2-like cytokines and, thereby, promote local infiltration of the airways with eosinophils and other proinflammatory cells seen in the asthmatic state.

In conclusion, the present study has identified the presence and up-regulated expression of FcεRII receptors in atopic asthmatic-sensitized airway smooth muscle, and has further demonstrated that the latter phenomenon is associated with the induction of altered airway responsiveness in the atopic asthmatic sensitized state. While comparably up-regulated expression of the FcεRII receptor has been demonstrated in different bone marrow-derived circulating leukocytes in atopic asthmatic individuals (Williams et al., 1992, J. Immunol. 149:2823–2829; Gagro et al., 1993, Int. Arch. Allergy Immunol. 101:203–208; Rabatic et al., 1993, Exp. Immunol. 94:337–340; Joseph et al., 1983, J. Clin. Invest. 71:221–230), the present observations raise a novel consideration regarding the pathobiology of asthma.

Accordingly, given the important immunological and proinflammatory responses attributed to FcεRII receptor activation, the present findings identify an important role and mechanism for the resident airway smooth muscle in autologously inducing its own IgE-mediated state of altered responsiveness contributing to the atopic asthmatic condition.

EXAMPLE 2

Expression of Low Affinity IgE Receptor, FcεRII, in Human Asthmatic ASM

The data disclosed elsewhere herein demonstrate, for the first time, the presence of Fc receptors in ASM tissue and cultured ASM cells, and that specific activation of FcεRII in rabbit ASM is associated with the induction of pro-asthmatic changes in agonist-mediated ASM constrictor and relaxant responsiveness. The experiments disclosed herein explore whether expression of specific Fc receptors is altered in inherently asthmatic human ASM tissue, and whether such altered expression represents a potentially inducible phenomenon in naive human ASM that is passively sensitized with human atopic asthmatic serum or IgE immune complexes.

The data disclosed herein demonstrate that: 1) while Fcγ receptor subtype expression is present and similar in both isolated control and inherently atopic asthmatic ASM, expression of the low-affinity receptor for IgE (FcεRII) is relatively markedly upregulated in the asthmatic tissue; 2) qualitatively comparable selective upregulation of FcεRII expression is inducible in naive (control) ASM passively sensitized with human atopic asthmatic serum or IgE immune complexes; and 3) the latter inducible phenomenon is associated with the autologous FcεRII-coupled release of the pro-inflammatory cytokine, IL-1β, by the sensitized ASM.

The Materials and Methods used in the experiments presented in this Example are now described.

Preparation of Human ASM Tissue

Human airway smooth muscle (ASM) tissue (both tracheal and bronchial sections) was isolated from a 12 year old asthmatic male who died from status asthmaticus (patient #1). While the patient's cardiopulmonary status responded to resuscitation, he was determined to be deceased based on brain perfusion scan criteria.

The lung and airway tissue were freshly obtained under sterile conditions during a subsequent organ donation procedure. The ASM tissue was carefully cleaned of loose connective tissue and epithelium under a microscope, prepared for RNA and protein extraction, and examined for Fc receptor expression, as described below. ASM tissue was also prepared from a 25 year old African-American female with asthma who died from an exacerbation complicated by a pneumonia (patient #2). Of note, microscopically, the airway tissue specimens from both patients exhibited all of the characteristic features of asthmatic airway tissue, including the presence of ASM hypertrophy/hyperplasia. Age-matched ASM tissue from six individuals who had no history of asthma and who either had a lung resection, or who died from non-pulmonary related causes, served as controls. The latter tissue specimens were tumor-free and microscopically normal.

In extended experiments, ASM tissue from three of the above six non-asthmatic subjects was passively sensitized with either human control serum, atopic asthmatic serum, IgE alone (2–15 μg/ml), or IgE immune complexes (2–15 μg IgE; 1–5 mg anti-IgE per ml), for various time points. The atopic asthmatic serum was obtained from allergic patients with moderate to severe asthma and serum IgE levels >1,000 IU/ml and 4–5/6 plus radioallergosorbent test (RAST) positive (specific IgE concentration of >17.5 Phadebas RAST Units (PRU)/ml) to *Dermatophagoides pteronyussinus, D. farinae*, and ragweed and positive skin test to these antigens. The control serum was obtained from nonatopic, nonasthmatic subjects with normal IgE levels (i.e., <70 IU/ml) and negative skin test reactivity, including to *Dermatophagoides pteronyussinus, D. farinae*, and ragweed. Protein and mRNA was isolated from the tissues for analysis of Fc receptor mRNA and protein expression. The participation of human subjects in this study was approved by the Institutional Review Board of the Joseph Stokes, Jr. Research Institute at the Children's Hospital of Philadelphia.

Preparation and Sensitization of Human Airway Smooth Muscle Cells

To further examine Fc receptor regulation in ASM cells, cultured human bronchial smooth muscle (HBSM) cells were used which were obtained from Clonetics Co. (San Diego, Calif.). The HBSM cells were derived from two healthy male donors, 16 and 21 years old. The cells were carefully characterized with specific markers to confirm the ASM phenotype and to exclude contamination with other cell types according to the manufacture's protocol. The cells were grown in Smooth Muscle Basal Medium (SmBM) supplemented with 5% FBS, insulin (5 ng/ml), EGF (10 ng/ml; human recombinant), FGF (2 ng/ml; human recombinant), gentamycin (50 ng/ml), and amphotericin-B (50 ng/ml). The standard experimental protocol involved growing the cells to confluence in the above medium. The cells were then starved in unsupplemented SMBM (serum-free medium, SFM) for 24 hours at which time the cells were treated with either human control serum from non-a topic/ non-asthmatic subjects or serum from subjects with atopic asthma in the absence and presence (40 mg/ml) of an anti-CD23 monoclonal blocking antibody (anti-CD23 mAb). In other experiments, cells were treated with SFM alone or SFM in the presence of maximum effective concentrations of IgE or IgE immune complexes. The cells were then examined for Fc receptor mRNA and protein expression, as described below.

Determination of Fcγ and Fcε Receptor mRNA Expression

Total RNA was isolated from the above tissue and cell preparations using the modified guanidinium thiocyanate phenol-chloroform extraction method to include proteinase K (in 5% SDS) digestion of protein in the initial RNA pellet (Chomczynski and Sacchi, 1987, Anal. Biochem. 162:156–159). The concentration of each RNA sample was then determined spectrophotometrically. This procedure consistently produced yields of 15–25 μg of intact RNA per each tissue specimen under study or T-75 flask of HBSM cells.

To analyze for mRNA expression of the FcγRI, FcγRII, FcγRIII, $\Phi_{\chi\epsilon}$RI and $\Phi_{\chi\epsilon}$RII receptor subtypes, a RT-PCR protocol was used and human specific primers for these Fc receptor subtypes were as previously described elsewhere herein. That is, cDNA was synthesized from total RNA isolated from: 1) naive versus inherently atopic asthmatic human ASM tissue; and 2) human ASM tissue or ASM cells passively sensitized with either IgE alone, IgE immune complexes, human control serum or atopic asthmatic serum in the absence and presence of anti-CD23 mAb. cDNA from activated peripheral blood mononuclear cells served as positive controls for the individual Fcγ and Fcε receptor expression analyses. The cDNA was primed with oligo(dT) 12–18 and extended with Superscript II reverse transcriptase (Gibgo BRL, Gaithersburg, Md.). The polymerase chain reaction (PCR) was used to amplify Fc receptor specific products from each cDNA reaction using the following Fc receptor primer pairs, based on the published sequences of the human Fcγ-RI, FcγRII, FcγRIII, and FcεRI and FcεRII genes (Capel et al., 1994, Immunometh. 4:25–34, Kikutani et al., 1986, Cell 47:657–665, and included the following primer sets: FcγRIa ([SEQ ID NO:1] and [SEQ ID NO:2]); FcγRIIa,c ([SEQ ID NO:3] and [SEQ ID NO:4]); FcγRIII ([SEQ ID NO:7] and [SEQ ID NO:8]); FcεRII ([SEQ ID NO:9 and [SEQ ID NO:10]); ribosomal protein L7 ([SEQ ID NO:13 and [SEQ ID NO:14]); and FcεRI primers 5' primer 5'GGAACGGGAATTACCATCCT3' (SEQ ID NO:15) and 3' primer 5'AAAGACGATCATCGGGAACC3' (SEQ ID NO: 16) (the amplification product is 313 bp).

The cycling profile used was as follows: Denaturation: 95° C. for 1 minute; annealing: 52–62° C. for 1.0–1.5 minutes; and extension: 72° C. for 1–2 minutes and 34–40 cycles for the Fcγ-RI, -RII, -RIII and Fcε-RI and -RII receptor genes, and 26 cycles for the RPL7 gene. The number of cycles was determined to be in the linear range of the PCR products. The PCR reactions for the human Fcγ, Fcε and RPL7 primers were performed using equivalent amounts of cDNA prepared from 2.5 μg of total RNA. Equal aliquots of each PCR reaction were then run on a 1.2% agarose gel and subsequently transferred to a Zeta-probe membrane overnight in 0.4 N NaOH. Following capillary transfer, the DNA was immobilized by UV-crosslinking using a Stratalinker UV Crosslinker 2400 at 120,000 microjoules/cm2 (Stratagene). Prehybridization in a Techne hybridization oven was conducted for 2–3 hours at 42° C. in 50% formaldehyde, 7% (w/v) SDS, 0.25 M NaCl, 0.12 M $Na_2HPO_4$ (pH 7.2), and 1 mM EDTA. Hybridization was for 20 hours at 42° C. in the same solution. The Fcγ-RI, -RII, -RIII, Fcε-RI and -RII and RPL7 DNA levels were assayed by Southern blot analysis using $^{32}$P-labeled probes. These probes were prepared by pooling several RT-PCR reactions for the individual Fc and RPL7 PCR fragments and purifying them from a 1.2% agarose gel using the Qiaex II agarose gel extraction kit. The individual Fc receptor cDNA fragments were subsequently sequenced for product confirmation. Washes were as follows: 1×15 minutes in 2×SSC, 0.1% SDS; 1×15 minutes in 0.1×SSC, 0.1% SDS both at room temperature, and 2×15 minutes at 50° C. in 0.1×SSC, 0.1% SDS. Southern blots were quantitated by direct measurements of radioactivity in each band using a PhosphoImager (Molecular Dynamics).

Fifteen μg of cytoplasmic RNA pertaining to each time point was also fractionated in 1% agarose, formaldehyde denaturing gels. Following capillary transfer, crosslinking and prehybridization, the levels of mRNA were analyzed using the above $^{32}$P-labeled cDNA fragments for the individual Fc receptor genes prepared by random priming, as previously described in (Hakonarson et al., 1997, J. Clin. Invest. 99:117–124). Northern blots were quantitated by direct measurement of radioactivity in each band using the PhosphoImager.

Determination of Fcγ and $\Phi_{\chi\epsilon}$ Receptor Protein Expression

Expression of cell surface protein for the FcγRI, FcγRII, FcγRIII and FcεRII receptors was assayed by Western blot analysis of membrane protein samples isolated from naive (control) and human asthmatic ASM tissue. The membrane protein samples were prepared from trachealis muscle that was microscopically cleaned of loose connective tissue and epithelium. The ASM was then minced and homogenized using a Wheaton dounce tissue grinder in 40 volumes of 50 mM tris(hydroxymethyl) aminomethane (Tris).HC1, 150 mM NaCl, 1 mM EDTA (pH 7.4) containing 1 mM phenyl-methylsulfonyl fluoride, 5 μg/ml aprotinin, and 5 μg/ml leupeptin. Nuclei and large particulates were removed by centrifugation at 100×g for 5 minutes. The supernatant was then centrifuged at 100,000×g for 1 hour to pellet the membrane fractions. The membrane pellet was resuspended in the same Tris.EDTA buffer, and the protein concentration was measured using the Lowry assay.

Equivalent amounts (30–50 μg) of membrane protein were fractionated in 11% sodium dodecyl sulfate (SDS)-polyacrylamide gels followed by transfer to nitrocellulose membranes. The membranes were then blotted overnight at room temperature in 25 mM Tris.HCl (pH 7.5), 150 mM NaCl, and 0.05% Tergitol NP-40 containing 5% nonfat milk, as previously described in (Hakonarson et al., 1995, Am. J. Physiol. (Lung Cell Mol. Physiol.) 269:L645–L652). The primary mouse anti-human FcγRI, FcγRII, FcγRIII and FcεRII antibodies used were diluted 1:250–500 and incubated for 1 hour at room temperature. All primary and secondary antibody incubations and washes were done in 25 mM Tris.HCl (pH 7.5), 150 mM NaCl, and 0.05% NP-40 containing 0.5% nonfat milk. The individual Fc receptor levels were detected using enhanced chemiluminescence after a 1 hour incubation with a 1:1,000 dilution of an anti-mouse horseradish peroxidase-linked secondary antibody and subsequent exposure to autoradiography film. Expression levels of the individual Fc receptor proteins were quantitated using laser densitometry (Bio-Rad, Hercules, Calif.).

Fc receptor cell surface expression was also examined in human ASM cells by flow cytometric analysis, using a Coulter EPICS Elite flow cytometer (Coulter EPICS Division, Hialeah, Fla.) equipped with a 5 watt argon laser operated at 488 nM and 300 mwatt output. Fluorescence signals were accumulated as two parameter fluorescence histograms with both % positive cells and mean channel fluorescence being recorded. Cells treated for 24 hours with either 20% human control serum or 20% human atopic asthmatic serum were resuspended in buffer, dispersed by passage through a 23 gauge needle, and then separately stained with primary mouse anti-human antibodies specific for the individual Fcγ-RI, -RII, -RIII and Fcε-RI and -RII receptor proteins (Serotec, Raleigh, N.C.) in 1:250–500 dilution. After subsequent repeat washing, FITC-labeled F(ab')2 goat anti-mouse IgE and IgG fragments were used as secondary antibodies and incubated for 1 hr in 1:500–1000 dilutions in PBS containing 0.5% BSA. Activated peripheral blood lymphocytes isolated from blood donors were used as the positive controls for the Fc receptor expression assays. The cells were also stained with mouse antibodies of the identical isotypes as the Fc receptor monoclonals to measure background fluorescence (i.e., mouse $IgG_1$ negative control). The antibody-stained cells were then evaluated by flow cytometry and analyzed using the Elite Immuno 4 statistical software (Coulter EPICS Division, Hialeah, Fla.). Fluorescence intensities were expressed as % positive cells, including mean channel fluorescence.

Additionally, an immunofluorescence detection assay was also used to examine for FcεRII surface receptor expression in ASM cells following 24 hour treatment with human control versus atopic asthmatic serum, as described above. Following standard preparation, the ASM cells were fixed in acetone and then mounted on poly-L-lysine coated slides. The cells were incubated with PBS buffer containing 10% human serum to suppress non-specific staining and the cells were subsequently labeled overnight at 4° C. with primary mouse anti-human CD23 antibody in 1:250 dilution. In control sections, the primary antibody was replaced by immunoglobulins of the same isotype following the manufacturer's protocol (mouse IgG1 negative control). Parallel cell slides were also stained with an α-actin antibody to exclude contamination of the ASM cells with non-actin containing cells. After subsequent repeat washing, FITC-labeled F(ab')2 goat anti-mouse IgE or IgG fragments were used as secondary antibodies, as described above. After serial washing, the slides were examined using a fluorescent microscope, and quantitative analysis of the protein localization in the cell and tissue sections under the above experimental conditions was performed using the Metamorph Imaging System (Universal Imaging Corp., West Chester, Pa.) interfaced with a Nikon Diaphot 300 Image Analyzer (Medville, N.Y.) that utilizes a Hamamatsu CCD camera (Tokyo, Japan).

ELISA Measurements of IL-1β Protein

Interleukin-1β (IL-1β) protein levels were measured in the culture media from microscopically isolated human ASM tissues at baseline and following 24 hours exposure to maximum effective concentrations of either IgE alone, IgE immune complexes, human control serum or human atopic asthmatic serum in the absence and presence of anti-CD23 mAb. IL-1β protein was quantitatively assessed using an enzyme specific immunoassay, as previously described (Hakonarson et al., 1997, J. Clin. Invest. 99:117–124). The latter assay was performed using a double antibody sandwich strategy in which an acetylcholine-esterase (AChE), Fab conjugated IL-1β-specific secondary antibody is targeted to a first cytokine-captured antibody. The enzymatic activity of the ACHE was measured spectrophotometrically and, relative to a linear standard curve (range: 0–250 pg/ml), the results were used to quantify the amount of the targeted IL-1β present in the tissue culture media.

Statistical Analysis

Statistical analysis was performed by means of the two-tailed paired Student's t-test. P-values <0.05 were considered significant.

Reagents

The human airway tissue was provided by the Cooperative Human Tissue Network which is funded by the National Cancer Institute. The human ASM cells and SMBM medium were obtained from Clonetics (Walkersville, Md.). The FcγRI, FcγRIIAC, FcγRIIB, FcγRIII, FcεRI, FcεRII and RPL7 primers were obtained from Integrated DNA Technologies Inc. (Coralville, Iowa). The human myeloma IgE and the goat-antihuman IgE antibodies were purchased from Biodesign, Int. (Kennebunk, Me.). The Fcγ-RI, -RII, -RIII and FcεRII monoclonal antibodies and the F(ab')2-FITC fragments used in protein assay studies were purchased from Serotec (Raleigh, N.C.). The anti-CD23 monoclonal blocking antibody (mAb135) is described in Mossalayi et al. (1002, EMBO J. 11:43234328).

The Results of the experiments presented herein are now described.

Fc Receptor mRNA Expression in Inherently Asthmatic and Atopic Asthmatic Serum-sensitized ASM To examine the expression of different Fc receptors in human ASM tissue and to determine whether this expression is altered in inherently atopic asthmatic ASM, RT-PCR incorporating Fc receptor specific primers for the different Fcγ and Fcε receptor subtypes was performed. Southern blots were then generated and probed with human cDNA probes specific for the individual Fcγ and Fcε receptor genes. A 157-bp RPL7 probe was also used to control for gel loading, and the signals for the Fcγ, Fcε and RPL7 PCR products were quantitated on a PhosphoImager. As shown in FIG. 11, ASM tissue expressed mRNA for all three Fcγ receptor subtypes and there were no significant differences in the magnitudes of the signals for either Fcγ-RI, -RII, or RIII between control (non-atopic/non-asthmatic) and inherently asthmatic ASM. Contrasting these observations, expression of the high affinity IgE receptor, FcεRI, was undetectable in either the control or asthmatic ASM tissue specimens (FIG. 12). mRNA expression of the low affinity IgE receptor, FcεRII (i.e., CD23), however, was present in both the control and asthmatic ASM tissues and, relative to the control ASM, the FcεRII signal was markedly upregulated in the asthmatic ASM (FIG. 12).

To determine whether the above selectively upregulated expression of FcεRII mRNA in the inherently atopic asthmatic ASM tissues potentially represented an inducible phenomenon, similar to that recently reported in rabbit ASM passively sensitized with human atopic asthmatic serum (Hakonarson and Grunstein, 1998, Proc. Natl. Acad. Sci. USA. 95:5257–5262), comparable experiments were conducted on adjacent segments of human control (non-atopic/non-asthmatic) ASM tissue sections that were passively sensitized for 24 hours with either human control or atopic asthmatic serum. Subsequent Southern blot analysis demonstrated that, while the FcεRII signal was barely detectable in the control serum-treated tissues, expression of FcεRII was markedly induced in the atopic asthmatic serum-sensitized ASM. In contrast, the constitutively expressed RPL7 signal was similar in both tissue preparations (FIG. 13).

In light of the above results, together with the data disclosed earlier regarding pharmacodynamic evidence demonstrating a critical role for immune-complexed IgE/CD23 interaction in mediating pro-asthmatic changes in ASM responsiveness in atopic asthmatic serum-sensitized tissues, the question of whether the observed upregulation of FcεRII expression in the atopic asthmatic serum-sensitized state was associated with IgE-coupled activation of the FcεRII receptor itself was examined. Using ASM tissue sections microscopically isolated from the same human tracheal and bronchial specimens, it was discovered that whereas the tissue samples exposed to atopic asthmatic serum (SE) displayed markedly induced FcεRII expression relative to the control (CO) serum-treated samples, this upregulation of FcεRII expression was largely prevented by pretreating the atopic serum-sensitized tissues with a monoclonal anti-CD23 blocking antibody (SE$^+$) (FIG. 14A). Moreover, in complimentary experiments examining the effects of exogenous administration of either human IgE alone or IgE immune complexes to naive ASM tissues, it was demonstrated that treatment of the tissues for 24 hours with IgE immune complexes induced a pronounced upregulated expression of FcεRII mRNA, whereas the corresponding RPL7 signal was unaffected (FIG. 14B). Comparably, exogenous administration of IgE alone had a qualitatively similar effect on FcεRII expression, however, the magnitude of this effect was relatively modest.

Fc Receptor Protein Expression in Inherently Asthmatic and Atopic Asthmatic Serum-sensitized ASM Cell surface expression of the Fc receptors, FcγRI, FcγRII, FcγRIII and FcεRII was also examined using Western immunoblot analysis of membrane protein samples isolated from human naive (control) and inherently asthmatic ASM tissues. As demonstrated in FIG. 15, protein expression signals were detected for the FcγRI, FcγRII and FcγRIII receptors, and there were no discernable differences in these signals between the control and asthmatic ASM tissues. In contrast, while FcεRII protein expression was virtually undetectable in the control ASM, the expression of FcεRII receptor protein was significantly upregulated in the asthmatic ASM (FIG. 15).

Given the above-disclosed data, in extended flow cytometric experiments, the question of whether cultured human ASM cells also express cell surface protein for the FcγRI, FcγRII, FcγRIII and FcεRII receptor subtypes, and whether this expression is altered following passive sensitization of the cells with atopic asthmatic serum was examined. As shown in FIG. 16, ASM cells expressed surface proteins for the above Fc receptor subtypes (FIG. 16A), and there were no differences in the expression signals for the Fcγreceptors between cells that were exposed to either control serum, atopic asthmatic serum, or serum-free medium. In contrast to unaltered Fcγreceptor expression, relative to control cells, 24 hours exposure of the ASM cells to atopic asthmatic serum induced upregulated cell surface expression of the FcεRII receptor (FIG. 16B).

To further substantiate the latter observations, the possible altered FcεRII receptor expression in atopic asthmatic serum-sensitized human ASM cells was examined by immunofluorescence staining. As shown in FIG. 17, relative to the isotype negative control antibody (upper panels), staining with a fluorescent-labeled anti-CD23 antibody was weakly positive in the control (CO) serum-treated cells (left panel). Conversely, and in accordance with the above flow cytometric analysis, immunofluorescence staining for the CD23 receptor protein was notably enhanced in the atopic asthmatic serum-treated ASM cells (right panel).

Taken together, and without wishing to be bound by theory, the data disclosed herein demonstrate that: 1) human ASM expresses mRNAs and protein for the FcγRI, FcγRII, and FcγRIII receptors for IgG, as well as the FcεRII receptor for IgE; 2) relative to control ASM, the expression of FcεRII is selectively upregulated in asthmatic ASM, and; 3) upregulated FcεRII receptor expression can be induced in naive ASM following exposure of the tissue or cultured cells to either human atopic asthmatic serum or exogenously administered IgE immune complexes.

Release of IL-1β by Atopic Asthmatic Sensitized ASM

It was recently reported that IL-1β protein is elaborated by rabbit ASM tissue or cultured cells passively sensitized with human atopic asthmatic serum (Hakonarson et al., 1997, J. Clin. Invest. 99:117–124). To the extent that the latter release of IL-1β was found to act in an autocrine fashion to endogenously induce pro-asthmatic changes in ASM responsiveness (Hakonarson et al., 1997, J. Clin. Invest. 99:117–124, Hakonarson et al., 1996, J. Clin. Invest. 97:2593–2600), it was next determined whether IgE immune complex-treated or atopic asthmatic serum-sensitized human ASM depicts altered IL-IB protein release. The latter was analyzed using an enzyme-specific immunoassay. There were no detectable levels of IL-1β protein in the culture media of ASM tissues exposed for 24 hours to vehicle or IgE alone. In contrast, tissues that were exposed to immune-complexed IgE (FIG. 18A) or atopic asthmatic serum (FIG. 18B) demonstrated markedly enhanced elaboration of IL-1β protein into the culture media at 8 and 24 hours. Moreover, this induced release of IL-1β was largely inhibited by pretreating the sensitized tissues with an anti-CD23 monoclonal blocking antibody (FIG. 18B), implicating a role for FcεRII activation in mediating the release of IL-1β in the sensitized state.

As stated previously elsewhere herein, bronchial asthma is characterized by exaggerated agonist-induced bronchoconstriction, attenuated beta-adrenoceptor-mediated airway relaxation and airway inflammation, the latter most notably involving infiltration of the airways with eosinophils and lymphocytes (Litchfield and Lee, 1992, J. Asthma. 29:181–191, Barnes et al., 1998, Pharmacol. Rev. 40:49–84, Kay, 1991, J. Allergy Clin. Immunol. 87:893). While the mechanistic interplay between inflammation and the associated changes in airway responsiveness remains to be identified, it is relevant to note that the altered airway responsiveness in asthmatic individuals has been associated with elevations in total and antigen-specific serum IgE (Sears et al., 1991, N. Engl. J. Med. 325:1067–1071, Burrows et al., 1989, N. Engl. J. Med. 320:272–277). Moreover, genetic analyses of family members with allergic asthma have demonstrated a significant correlation between altered airway responsiveness and serum IgE levels (Burrows et al., 1995, Am. J. Respir. Crit. Care Med. 152:1497–1500, Burrows et al., 1995, J. Allergy Clin. Immunol. 95:548–556).

Without wishing to be bound by theory, these findings suggest a mechanistic relationship between serum IgE levels and changes in airway responsiveness in atopic asthma. Indeed, it is well established that IgE can induce an immediate hypersensitivity reaction in the airways following allergen exposure, and that this acute bronchoconstriction is initiated by degranulation of mast cells following activation of their high affinity IgE receptor, FcεRI (Metzger, 1992, Immunol. Rev. 125:37–48, Beaven and Metzger, 1993, Immunol. Today 14:222–226, Galli, 1993, N. Eng. J. Med. 328:257–265, Matsumoto et al., 1987, Annal. Allergy. 58:261). Furthermore, progression of the initial IgE/FcεRI-coupled mast cell response into the late phase asthmatic response has been largely attributed to the orchestrated extended release of various cytokines by other stimulated infiltrating inflammatory cell types (Beaven and Metzger, 1993, Immunol. Today. 14:222–226, Beasley et al., 1989, Am. Rev. Respir. Dis. 139:806, Litchfield and Lee, 1992, J. Asthma. 29:181–191, Walker et al., 1992, Am. Rev. Respir. Dis. 146:109–115). In this regard, it has been recently demonstrated that expression of the inducible form of the low affinity IgE receptor (FcεRII) is upregulated on monocytes and lung alveolar macrophages (William et al., 1992, J. Immunol. 149:2823–2829), as well as on circulating B lymphocytes isolated from atopic asthmatic subjects (Chihara et al., 1991, Annal. Allergy. 67:429, Gagro et al., 1993, Int. Arch. Allergy. Immunol. 101:203–208, Rabatic et al., 1993, Exp. Immunol. 94:337–340). Thus, apart from mast cells per se, IgE/Fcε receptor interactions involving other bone-marrow-derived pro-inflammatory cells may also contribute to the allergic asthmatic pulmonary response.

The data presented elsewhere herein disclose, for the first time, the presence of Fc receptors in airway smooth muscle tissue and cultured ASM cells, and establish that specific activation of FcεRII in rabbit ASM is associated with the induction of pro-asthmatic changes in agonist-mediated ASM constrictor and relaxant responsiveness (see Example 1, supra). In light of these findings, the study presented in the present Example further investigated whether expression of specific Fc receptors is altered in inherently asthmatic human ASM tissue, and whether such altered Fc receptor expression represents a potentially inducible phenomenon in naive human ASM that is passively sensitized with human atopic asthmatic serum or IgE immune complexes. The data disclosed herein demonstrate that while Fcγ receptor subtype expression is present and similar in both isolated control and inherently atopic asthmatic ASM, expression of the low-affinity receptor for IgE, FcεRII, is markedly upregulated in the asthmatic tissue compared with its expression in control ASM. Further, the data disclosed herein demonstrate that qualitatively comparable selective upregulation of FcεRII expression is inducible in naive (control) ASM passively sensitized with human atopic asthmatic serum or with IgE immune complexes. Moreover, the data disclosed show that the upregulation of FcεRII expression induced by treatment of naive ASM with IgE immune complexes is associated with the autologous FcεRII-coupled release of the pro-inflammatory cytokine, IL-1β, by the sensitized ASM.

It is relevant, in light of the instant disclosure, to note that in addition to the reported upregulation of FcεRII expression on monocytes, lung alveolar macrophages (William et al., 1992, J. Immunol. 149:2823–2829), and circulating B lymphocytes isolated from atopic asthmatic individuals (Chihara et al., 1991, Annal. Allergy. 67:429, Gagro et al., 1993, Int. Arch. Allergy. Immunol. 101:203–208, Rabatic et al., 1993, Exp. Immunol. 94:337–340), exposure of asthmatic subjects to allergen and treatment of isolated monocytes with specific cytokines have both been shown to upregulate FcεRII expression on mononuclear phagocytes (William et al., 1992, J. Immunol. 149:2823–2829, Joseph et al., 1983, J. Clin. Invest. 71:221–230). These findings are in agreement with the data disclosed herein, and further support that upregulated FcεRII expression may play an important role in establishing the pro-inflammatory changes in the airway that characterize the atopic asthmatic state and may be important in the treatment of asthma and the development effective therapeutics therefor. Moreover, without wishing to be bound by theory, the data disclosed herein demonstrating altered FcεRII expression in inherently asthmatic ASM, suggest that, apart from an implied role(s) for infiltrating leukocytes, the upregulated expression of FcεRII in ASM may also serve to foster the pro-asthmatic phenotype. In addition, the data disclosed herein demonstrating that the induced pro-asthmatic changes in constrictor and relaxant responsiveness in rabbit ASM passively sensitized with human atopic asthmatic serum or IgE immune complexes is preventable by pretreating the sensitized ASM with a monoclonal anti-CD23 blocking antibody (see Example 1, supra) further support the involvement of upregulated expression of FcεRII in ASM in fostering the pro-asthmatic phenotype.

In addressing the mechanism underlying the increased expression of FcεRII in inherently atopic asthmatic ASM, the data disclosed herein indicate that this increased expression may represent an inducible phenomenon in naive human ASM. Indeed, exposure of naive human ASM tissue to either atopic asthmatic serum or IgE immune complexes induced comparably increased FcεRII receptor expression in the sensitized ASM. Moreover, the data disclosed herein demonstrate that this experimentally-induced upregulated expression of FcεRII was largely prevented by pretreating the human ASM tissue with an anti-CD23 blocking antibody (FIGS. 14A and 14B). Thus, the data disclosed herein support the presence of an IgE/CD23-dependent mechanism that autologously regulates FcεRII expression in sensitized human ASM. This concept is in accordance with a number of earlier studies which have reported a direct correlation between serum IgE levels and FcεRII and -RI expression in other cell types (Spiegelberg and Simon, 1981, J. Clin. Invest. 68:845–852; Conroy et al., 1977, J. Immunol. 118:1317–1324; Malveaux et al., 1978, J. Clin. Invest. 62:176–181). Although these reports raised the notion of a possible common mechanism regulating the production of both IgE and its receptors, more recent evidence based on studies using different cell lines suggests that IgE itself may enhance FcεRI (Lantz et al., 1997, J. Immunol. 158:2517–2521, Yamaguchi et al., 1997, J. Exp. Med. 185:663–67236) or FcεRII expression (Lee et al., 1987, J. Immunol. 139:1191–1198, Daeron and Ishizaka, 1986, J. Immunol. 136:1612–1619, Lee and Conrad, 1986, J. Immunol. 136:45734580). The data disclosed herein suggest the presence of a positive feedback system in human ASM wherein IgE upregulates the expression of its own low-affinity receptor. Moreover, the data disclosed herein demonstrate, for the first time, that ASM tissue and cells also exhibit an upregulation of FcεRII expression associated with the asthmatic phenotype which was unexpected given the fact that only bone marrow-derived cells (monocytes, macrophages, mononuclear phagocytes and B lymphocytes), have been previously shown to exhibit this phenomenon. The potential role(s) of these bone marrow-derived lymphocytes in the pathogenesis of the asthmatic state remains to be elucidated. In contrast, the data presented herein documents that the upregulated FcεRII expression in smooth muscle cells is directly responsible for the manifestation of the pro-asthmatic phenotype in the altered constriction and relaxation of smooth muscle. Since lymphocytes do not constrict, the relationship of the upregulation of this receptor on these cells to asthma is not known.

Studies in Example 1 herein, which examined the mechanistic link between exposure of naive rabbit ASM tissue to atopic asthmatic serum and its resultant altered agonist responsiveness, demonstrate that the induced pro-asthmatic changes in ASM responsiveness were initiated by IgE/FcεRII-coupled activation, associated with the induced autologous expression and autocrine action of IL-1β in the atopic sensitized ASM. Moreover, the mechanism of action of IL-1β in eliciting the pro-asthmatic changes in ASM responsiveness was attributed to its induced upregulated expression of Gi protein, specifically Giα$_2$ and Giα$_3$, which inhibit intracellular cAMP accumulation (Hakonarson et al., 1996, J. Clin. Invest. 97:2593–2600). The studies disclosed herein do not permit comparable examination of the above mechanism of altered responsiveness in human ASM tissue, due to its limited availability in quantity sufficient for pharmacodynamic experiments. Nevertheless, consistent with the mechanism identified in rabbit ASM (Example 1 herein), the data disclosed herein demonstrate that human ASM tissue passively sensitized with atopic asthmatic serum or IgE immune complexes exhibits markedly enhanced release of IL-1β protein into the culture medium (FIG. 18A). In addition, the data disclosed herein demonstrate that the latter induced release of IL-1β is largely prevented by pretreating the sensitized human ASM with an anti-CD23 blocking antibody (FIG. 18B). Thus, without wishing to be bound by theory, the data disclosed herein suggest that sensitized human ASM tissue may undergo pro-asthmatic changes in its responsiveness which are comparable to those seen in sensitized rabbit ASM.

In conclusion, the data disclosed herein demonstrate the presence and regulation of Fc receptors in inherently asthmatic human ASM tissue and in naive human ASM passively sensitized with human atopic asthmatic serum and IgE immune complexes. The results demonstrate that: 1) human ASM tissue expresses mRNA and surface protein for the low affinity receptor for IgE, FcεRII, as well as for the FcγRI, FcγRII and FcγRIII receptor subtypes that bind to IgG, whereas expression of the high-affinity receptor for IgE (FcεRI) is undetectable; 2) in contrast to unaltered Fcγ subtype expression, relative to naive (control) human ASM, expression of FcεRII mRNA and protein is significantly upregulated in inherently asthmatic ASM tissues; 3) upregulated expression of FcεRII represents, at least in part, an inducible phenomenon that is largely attributed to IgE immune complex-coupled activation of the FcεRII receptor itself; and 4) the latter action is associated with FcεRII-induced autologous elaboration of IL-1β protein by the ASM.

While comparably up-regulated expression of the FcεRII receptor has been demonstrated in different bone marrow-derived circulating leukocytes isolated from atopic asthmatic individuals (William et al., 1992, J. Immunol. 149:2823–2829, Chihara et al., 1991, Annal. Allergy. 67:429, Gagro et al., 1993, Int. Arch. Allergy. Immunol. 101:203–208, Rabatic et al., 1993, Exp. Immunol. 94:337–340), the present observations raise a novel consideration regarding the pathobiology of asthma. Accordingly, given the important immunological, proinflammatory and physiological responses attributed to FcεRII receptor activation, the present findings support the concept that upregulated FcεRII expression and action in human asthmatic ASM plays an important role in establishing its asthmatic phenotype.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for preventing induction of a CD23 mediated asthmatic state in a human patient comprising administering to airway smooth muscle cells of said human an agent which inhibits binding of IgE to FcεRII receptor protein, said agent being suspended in a pharmaceutically acceptable carrier in an amount sufficient to inhibit said binding of IgE to FcεRII receptor protein thereby preventing induction of said asthmatic state in said human.

2. The method of claim 1, wherein said agent which inhibits binding of IgE to FcεRII receptor protein is an anti-FCεRII receptor protein antibody.

3. The method of claim 1, wherein said agent is selected from the group consisting of a polyclonal antibody, a monoclonal antibody, a synthetic antibody, a chimeric antibody, and a humanized antibody.

4. The method of claim 1, wherein said agent is selected from the group consisting of an isolated protein, an isolated polypeptide and a non-peptide.

5. The method of claim 1 wherein said agent is administered to the human in an amount between about 1 ng/kg and about 100 mg/kg of patient body weight.

6. The method of claim 1, wherein said pharmaceutically acceptable carrier is physiological saline.

7. The method of claim 1, wherein said agent is administered in aerosol form.

8. The method of claim 1, wherein said agent is administered by inhalation.

9. The method of claim 1, wherein said agent is administered via a nebulizer.

10. The method of claim 1, wherein said agent is delivered to the lower trachea.

11. The method of claim 1, wherein said agent is delivered to the nasal tract or the upper respiratory tract.

12. The method of claim 1, wherein said agent is administered in conjunction with at least one agent selected from the group consisting of corticosteroid, sodium cromolyn, methylxanthine, leukotriene modifiers, anti-cholinergic agents, and beta adrenergic agents.

13. A method for causing the symptoms of asthma to diminish in a human patient comprising administering to airway smooth muscle cells of said human an agent which inhibits binding of IgE to FcεRII receptor protein, said agent being suspended in a pharmaceutically acceptable carrier in an amount sufficient to inhibit binding of IgE to FcεRII receptor protein thereby causing the symptoms of asthma to diminish.

14. The method of claim 13, wherein said agent is an anti-FcεRII receptor protein antibody.

15. The method of claim 13, wherein said agent is selected from the group consisting of a polyclonal antibody, a monoclonal antibody, a synthetic antibody, a chimeric antibody, and a humanized antibody.

16. The method of claim 13, wherein said agent is selected from the group consisting of an isolated protein, an isolated polypeptide and a non-peptide.

17. The method of claim 13, wherein said agent is administered to the human in an amount between 1 ng/kg and about 100 mg/kg of patient body weight.

18. The method of claim 17, wherein said pharmaceutically acceptable carrier is physiological saline.

19. The method of claim 13, wherein said agent is administered in aerosol form.

20. The method of claim 13, wherein said agent is administered by inhalation.

21. The method of claim 13, wherein said agent is administered via a nebulizer.

22. The method of claim 13, wherein said agent is delivered to the lower trachea.

23. The method of claim 13, wherein said agent is delivered to the nasal tract or the upper respiratory tract.

24. The method of claim 13, wherein said agent is administered in conjunction with at least one agent selected from the group consisting of corticosteroid, sodium cromolyn, methylxanthine, leukotriene modifiers, anticholinergic agents, and beta adrenergic agents.

* * * * *